United States Patent
Mackel et al.

(10) Patent No.: US 10,639,347 B2
(45) Date of Patent: *May 5, 2020

(54) PEPTIDES USEABLE FOR TREATMENT OF DISORDERS OF THE EYE

(71) Applicant: Allegro Pharmaceuticals, LLC, San Juan Capistrano, CA (US)

(72) Inventors: Michael John Mackel, Portland, OR (US); John Park, Santa Ana, CA (US)

(73) Assignee: Allegro Pharmaceuticals, LLC, San Juan Capistrano, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/420,068

(22) Filed: May 22, 2019

(65) Prior Publication Data

US 2019/0343916 A1 Nov. 14, 2019

Related U.S. Application Data

(63) Continuation of application No. 15/867,101, filed on Jan. 10, 2018, now Pat. No. 10,307,460, which is a continuation of application No. 14/696,250, filed on Apr. 24, 2015, now Pat. No. 9,872,886, which is a continuation of application No. 12/943,900, filed on Nov. 10, 2010, now Pat. No. 9,018,352.

(60) Provisional application No. 61/259,748, filed on Nov. 10, 2009.

(51) Int. Cl.

| | | |
|---|---|---|
| A61K 38/08 | (2019.01) |
| A61K 38/12 | (2006.01) |
| A61K 47/64 | (2017.01) |
| A61K 38/07 | (2006.01) |
| A61K 51/08 | (2006.01) |
| A61L 27/22 | (2006.01) |
| A61K 9/08 | (2006.01) |
| C07K 7/00 | (2006.01) |
| A61K 51/06 | (2006.01) |
| A61K 38/17 | (2006.01) |
| A61L 31/04 | (2006.01) |
| A61K 9/06 | (2006.01) |

(52) U.S. Cl.
CPC ............ *A61K 38/12* (2013.01); *A61K 9/08* (2013.01); *A61K 38/07* (2013.01); *A61K 38/1709* (2013.01); *A61K 47/64* (2017.08); *A61K 51/065* (2013.01); *A61K 51/082* (2013.01); *A61K 51/088* (2013.01); *A61L 27/227* (2013.01); *A61L 31/043* (2013.01); *C07K 7/00* (2013.01); *A61K 9/06* (2013.01); *A61L 2300/252* (2013.01)

(58) Field of Classification Search
None
See application file for complete search history.

(56) References Cited

U.S. PATENT DOCUMENTS

| | | |
|---|---|---|
| 4,517,686 A | 5/1985 | Ruoslahti et al. |
| 4,578,079 A | 3/1986 | Ruoslahti et al. |
| 4,589,881 A | 5/1986 | Pierschbacher et al. |
| 4,614,517 A | 9/1986 | Ruoslahti et al. |
| 4,661,111 A | 4/1987 | Ruoslahti et al. |
| 5,635,477 A * | 6/1997 | Degrado ............. C07K 7/56 514/14.9 |
| 6,087,330 A | 7/2000 | Kogan et al. |
| 6,331,285 B1 | 12/2001 | Sharma |
| 6,500,924 B1 | 12/2002 | Brooks et al. |
| 6,863,886 B2 | 3/2005 | Karageozian et al. |
| 7,070,936 B1 | 7/2006 | Hangauer et al. |
| 9,018,352 B2 | 4/2015 | Mackel et al. |
| 9,872,886 B2 | 1/2018 | Mackel et al. |
| 9,896,480 B2 | 2/2018 | Mackel et al. |
| 2002/0115823 A1 | 8/2002 | Wakimasu et al. |
| 2003/0059422 A1 | 3/2003 | Sharma |
| 2003/0139342 A1 | 7/2003 | McCuen et al. |
| 2003/0166004 A1 | 9/2003 | Gyuris et al. |
| 2003/0170250 A1 | 9/2003 | Ezrin et al. |
| 2004/0072315 A1 | 4/2004 | Lu et al. |
| 2006/0104898 A1 | 5/2006 | Hallahan et al. |
| 2006/0106196 A1 | 5/2006 | Gaudemack et al. |
| 2009/0088377 A1 | 4/2009 | Quraishi et al. |
| 2013/0129621 A1 | 5/2013 | Mackel et al. |
| 2015/0190459 A1 | 7/2015 | Tymianski |

(Continued)

FOREIGN PATENT DOCUMENTS

| | | |
|---|---|---|
| CN | 1849132 A | 10/2006 |
| JP | 08-119991 | 5/1996 |

(Continued)

OTHER PUBLICATIONS

Men, Rapid Commun. Mass Spectrom. 2005; 19: 23-30 (Year: 2005).*
Office Action dated Nov. 14, 2017 in related Australian Patent Application No. 2017204193.
Harris et al. 'Radiolabeled Divalent Peptidomimetic Vitronectin Receptor Antagonists as Potential Tumor Radiotherapeutic and Imaging Agents' Bioconjugate Chem (2007) vol. 18 p. 1266-1279; abstract, p. 1266, col. 2, para 1, Figs. 1-2, 11.
Li et al. '64Cu-Labeled Tetrameric and Octameric RGD Peptides for Small-Animal PET of Tumor alphavbeta3Integrin Expression' J Nuclear Medicine (2007) vol. 48 p. 1162-1171; abstract, Fig. 1.

(Continued)

*Primary Examiner* — Satyanarayana R Gudibande
(74) *Attorney, Agent, or Firm* — Robert D. Buyan; Stout, Uxa & Buyan, LLP

(57) ABSTRACT

Compounds comprising R-G-Cysteic Acid (i.e., R-G-NH—CH($CH_2$—$SO_3$H)COOH or Arg-Gly-NH—CH($CH_2$—$SO_3$H)COOH) and derivatives thereof, including pharmaceutically acceptable salts, hydrates, stereoisomers, multimers, cyclic forms, linear forms, drug-conjugates, prodrugs and their derivatives. Also disclosed are methods for making and using such compounds including methods for inhibiting cellular adhesion to RGD binding sites or delivering other diagnostic or therapeutic agents to RGD binding sites in human or animal subjects.

16 Claims, 5 Drawing Sheets

Specification includes a Sequence Listing.

(56) References Cited

U.S. PATENT DOCUMENTS

| | | |
|---|---|---|
| 2016/0022763 A1 | 1/2016 | Mackel et al. |
| 2016/0058881 A1 | 3/2016 | Dimarchi et al. |
| 2018/0207227 A1 | 7/2018 | Karageozian et al. |

FOREIGN PATENT DOCUMENTS

| | | |
|---|---|---|
| JP | 2002534132 A | 10/2002 |
| JP | 2002326949 | 11/2002 |
| WO | WO94/15953 A1 | 7/1994 |
| WO | WO94/20531 A1 | 9/1994 |
| WO | WO9422910 A1 | 10/1994 |
| WO | WO98/33494 A1 | 8/1998 |
| WO | WO9963084 A1 | 12/1999 |
| WO | WO2006017619 A2 | 2/2006 |
| WO | WO2008134761 A2 | 11/2008 |
| WO | WO2008/152508 A2 | 12/2008 |
| WO | WO2011/060104 A2 | 5/2011 |
| WO | WO2012/045719 A2 | 4/2012 |
| WO | WO2012/154894 A2 | 11/2012 |

OTHER PUBLICATIONS

Schornberg et al. 'a5b1-Integrin controls ebolavirus entry by regulating endosomal cathepsins' PNAS (2009) vol. 106, No. 19 p. 8003-8008; abstract.

Eichhom et al. 'Angiogenesis in cancer: molecular mechanisms, clinical impact' Langenbecks Arch Surg (2007) vol. 392 p. 371-379; p. 374, col. 2, para 2, p. 375, col. 2, para 2.

Miyamoto et al. 'Integrins Can Collaborate with Growth Factors for Phosphorylation of Receptor Tyrosine Kinases and Map Kinase Activation: Roles of Integrin Aggregation and Occupancy of Receptors' J Cell Biol (1996) vol. 135 p. 1633-1642; abstract.

Greene's Protective Groups in Organic Synthesis by Peter G.M. Wuts and Theodora W. Greene, (2nd edition) J. Wiley & Sons, 1991.

Hugo E. Sepulveda-Vazquez, et al., "Intravitreal Injection of Integrin Peptide ALG-1001 for the Induction of Posterior Vitreous Detachment in Rabbit Eyes", Investigative Ophthalmology & Visual Science, vol. ARVO, 2012.

"Allegro Ophthalmics Announces Presentation of Key Data on New Class of Vascular Eye Disease Therapy", Press Release.

Lisa D. Volk, et al., "Synergy of Nab-Paclitaxel and Bevacizumab in Eradicating Large Orthotopic Breast Tumors and Preexisting Metastases," Neoplasia, vol. 13, No. 4, Apr. 2011, pp. 327-338.

Gesine B. Jaissle M.D. et al., "Suppression of Melanoma-Associated Neoangiogenesis by Bevacizumab," Arch Dermatol, vol. 144, No. 4, Apr. 2008, pp. 525-527.

Jian-Ping Xiong et al., "Crytal Structure of the Extracellular Segment of Integrin αVβ3 in Complex with an Arg-Gly-Asp Ligand," Science, vol. 296, Apr. 2002, pp. 151-155.

Office Action dated Feb. 23, 2016 in corresponding Japanese Patent Application No. 2014-510451.

Extended European Search Report dated Oct. 16, 2017 in related European Application No. 17159955.8.

Office Action dated Jul. 28, 2015 in corresponding Japanese Patent Application No. 2012-538958.

Larson, Richard S. "Peptide Antagonists that Inhibit Sin Nombre Virus and Hantaan Virus Entry through the β3-Integrin Receptor", Journal of Virology, 2005, 79(12), 7319-7326.

Asymmetric Synthesis by Von G. M. Coppola and H. F. Schuster; John Wiley & Sons, New York 1987.

Knudson, W. et al, Matrix Bio. (2002), 21: 15-23.

Yoles, E., et al.; a2-Adrenoreceptor Agonists Are Neuroprotective in a Rat Model of Optic Nerve Degeneration; Investigative Ophthalmology & Visual Science, vol. 40, No. 1, pp. 65-73 (Jan. 1999).

Neufeld, A.H., et al.; Inhibition of Nitric-Oxide Synthase 2 by Aminoguanidine Provides Neuroprotection of Retinal Ganglion Cells in a Rat Model of Chronic Glaucoma; Proc. Natl. Acad. Sci. USA 96 (1999).

PCT International Search Report dated Aug. 23, 2018 in related PCT Application No. PCT/US2018/014287.

Lee, et al., "Light-triggered in vivo Activation of Adhesive Peptides Regulates Cell Adhesion, Inflammation and Vascularization of Biomaterials," Nature Materials, vol. 14, No. 3, Mar. 2015, pp. 352-360.

Suh et al., "An Angiogenic, Endothelial-Cell-Targeted Polymeric Gene Carrier," Molecular Therapy, vol. 6, No. 5, Nov. 2002, pp. 664-672.

Kristensen et al., "Primary Structure of Human $\alpha 2$-Macroglobulin," The Journal of Biological Chemistry, vol. 259, No. 13, Jul. 1984, pp. 8313-8317.

Lambert, V., et al., "Laser-Induced Choroidal Neovascularization Model to Study Age Related Macular Degeneration in Mice," Nature Protocols, vol. 8, No. 11, Nov. 2013, pp. 2197-2211.

Christine E. Schmidt et al., "Neural Tissue Engineering: Strategies for Repair and Regeneration," Annu. Rev. Biomed. Eng. 2003, 5:293-347.

Martina Santarelli et al., "Advances in Pharmacotherapy for Wet Age-Related Macular Degeneration," Expert Opin. Pharmacother., 2015, 16:1769-1781.

Haiwei H. Guo, et al., "Protein tolerance to random amino acid change," PNAS, 2004, 101:9205-9210.

Baruch D. Kuppermann, "A Dual Mechanism Drug for Vitreoretinal Diseases," Retina Today, Jul./Aug. 2015, pp. 85-87.

James U. Bowie et al., "Deciphering the Message in Protein Sequences: Tolerance to Amino Acid Substitutions," Scienc, 1990, vol. 247, No. 4948, pp. 1306-1310.

Aniruddha Agarwal et al., "Novel Therapies in Development for Diabetic Macular Edema," Current Diabetes Reports, 2015, published online DOI10.1007/s11890-015-9652-z.

Moulay Hicham Alaoui-Ismaili et al., "Design of Second Generation Therapeutic Recombinant Bone Morphogenetic Proteins," Cytokine & Growth Factor Reviews, 20 (2009) pp. 501-507.

Wilson H. Burgess, et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," Journal of Cell Biology, vol. 111, Nov. 990, pp. 2129-2138.

Andrew R. Blight,"Miracles and Molecules—Progress in Spinal Cord Repair," Nature Neuroscience Supplement, vol. 5, Nov. 2002, pp. 1051-1054.

Bert A. 't Hart et al., "The Use of Animal Models to Investigate the Pathogenesis of Neuroinflammatory Disorders of the Central Nervous System," Current Opinion in Neurology, 2003, 16:375-383.

Ahmet Hoke, "Mechanisms of Disease: What Factors Limit the Success of Peripheral Nerve Regeneration in Humans?" Nature Clinical Practice Neurology, Aug. 2006, vol. 2, No. 8, pp. 448-454.

Tony Pawson et al., "Assembly of Cell Regulatory Systems Through Protein Interaction Domains," Science, vol. 300, Apr. 2003 pp. 445-452.

PCT International Search Report dated Sep. 24, 2018 in related PCT Application No. PCT/US2018/038365.

PCT International Search Report dated Aug. 14, 2012 in related PCT Application No. PCT/US2012/037177.

K.G. Schmidt et al., "Neurodegenerative Diseases of the Retina and Potential for Protection and Recovery," Current Neuropharmacology, 2008, vol. 6, pp. 164-178.

The factsheet of the clinical trials of AG-101 from the Allegro Ophthalmics data from the Allegro website: www.allegroeye.com/allegro-ophthalmics-begins-phase-2-clinical-trial-of-luminate-alg-1001-for-the-treatment-of-diabetic-macular-edema/retrieved on Sep. 16, 2019.

PCT International Search Report dated Sep. 22, 2011 in related PCT Application No. PCT/US2010/056277.

Chen et al., "Synthesis and Biological Evaluation of Dimeric RGD Peptide-paclitaxel conjugate as a Model for Integrin-Targeted Drug Delivery", J. Med. Chem., vol. 48, No. 4, Feb. 24, 2005, pp. 1098-1106.

Verstraeten, Thierry C. et al., "Pharmacologic Induction of Posterior Vitreous Detachment in the Rabbit," Arch. Ophthalmol, vol. 111, 1993.

(56) References Cited

OTHER PUBLICATIONS

Foos, R Y., "Vitreoretinal juncture; topographical variations", Invest. Opthalmol. Vis. Sci. (1972) vol. 11 No. 10, 801-808.

Hershkoviz, S. M., et al., "Nonpeptidic Analogues of the Arg-Gly-Asp (RGD) Sequence Specifically Inhibit the Adhesion of Human Tenon's Capsule Fibroblasts to Fibronectin," Invest. Ophthalmol. Vis. Sci., (1994), vol. 35, No. 5, 2585-2591.

Jiang, D. et aL, "Hyaluronan in Tissue Injury and Repair," Annu. Rev. Cell. Dev. Biol. (2007) 23: 435-461.

Hiroshi Mochimaru et al., "Involvement of Hyaluronan and Its Receptor CD44 with Choroidal Neovascularization," Invest. Ophthalmol. Vis. Sci. (2009) vol. 50, No. 9: 4410-4415.

Michael A. Dechantsreiter et al., "N-Methylated Cyclic RGD Peptides as Highly Active and Selective $\alpha v\beta 3$ Integrin Antagonists," J. Med. Chem. (1999) 42:3033-3040.

Elner, S.G.,et al., "The Integrin Superfamily and the Eye," IOVS (1996) vol. 37, No. 5:696-701.

M. A. Buerkle et al., "Inhibition of the alpha-v integrins with a cyclic RGD peptide impairs angiogenesis, growth and metastasis of solid tumors in vivo," British J. Cancer (2002) 86: 788-795.

Eileen M. Finnegan et al., "Small-molecule cyclic $\alpha v\beta 3$ antagonists inhibit sickle red cell adhesion to vascular endothelium and vasoocclusion," Am. J. Physiol. Heart Circ. Physiol., (2007) 293: H1038-H1045.

Pina M. Cardarelli et al., "Cyclic RGD Peptide Inhibits $\alpha 4\beta 1$ Interaction with Connecting Segment 1 and Vascular Cell Adhesion Molecule," J. Biol. Chem. (1994) vol. 269, No. 28:18668-18673.

H.D. Maynard, J.A. Hubbell, "Discovery of a sulfated tetrapeptide that binds to vascular endothelial growth factor,"Acta Biomaterialia (2005) 1:451-459.

Ruoslahti, E., "Integrins," J. Clin. Invest. (1991) vol. 87: 1-5.

Li, Z. et al., 64CU-Labeled Tetrameric and Octameric RGD Peptides for Small-Animal PET of Tumor $\alpha v\beta 3$ Integrin Expression; J. Nucl. Med. vol. 48, pp. 1162-1171 (2007).

Sebag, J., "Anatomy and Pathology of the Vitreo-Retinal Interface," Eye (1992), 6: 541-552.

Hynes, R.A., et al., "Contact and Adhesive Specificities in the Associations, Migrations, and Targeting of Cells and Axons," Cell (1992) 68: 303-322.

Kelly, N-E., et al., "Vitreous Surgery for Idiopathic Macular Holes," Arch. Ophthalmol. (1991) 109, 654-659.

Humphries, M.J., "The molecular basis and specificity of integrin-ligand interactions," J. Cell Sci., (1990) 97: 585-592.

Nip, J., et al., "Human Melanoma Cells Derived from Lymphatic Metastases Use Integrin $\alpha v\beta 3$ to Adhere to Lymph Node Vitronectin," J. Clin. Invest., (1992) 90: 1406-1413.

Han, D.P., et al., "Surgical Excision of the Attached Posterior Hyaloid," Arch. Ophthalmol. (1998) 106: 998-1000.

Trese, M.T., "Enzymatic-assisted vitrectomy," Eye. (2002) 16: 365-368.

Gandorfer, A., et al., "Vitreoretinal Morphology of Plasmin-Treated Human Eyes," Am. J. Ophthalmol. (2002) 133: 156-159.

Hesse, L., et al., "Induction of Posterior Vitreous Detachment in Rabbits by Intravitreal Injection of Tissue Plasminogen Activator Following Cryopexy," Eye Res. (2000) 70: 31-39.

Rong, L. et al., "Integrin $\alpha 5\beta 1$ Mediates Attachment, Migration, and Proliferation in Human Retinal Pigment Epithelium: Relevance for Proliferative Retinal Disease," Invest. Ophthalmol. Vis. Sci. (2009) 50: 5988-5996.

Nickerson, C., et al., "Rheological properties of the vitreous and the role of hyaluronic acid," J. Biomechanics, (2008) 41: 1840-1846.

Peter C. Brooks, et al., "Antiintegrin $\alpha v\beta 3$ blocks human breast cancer growth and angiogenesis in human skin," J. Clin. Invest., (1995) 96: 1815-1822.

Leonardo B. Oliveira, et al., "RGD peptide-assisted vitrectomy to facilitate induction of a posterior vitreous detachment: A new principle in pharmacological vitreolysis," Curr. Eye Res. (2002) 25: 333-340.

Lehmann, M. et al., "A Monoclonal Antibody Inhibits Adhesion to Fibronectin and Vitronectin of a Colon Carcinoma Cell Line and Recognizes the Integrins $\alpha v\beta 3$, $\beta v\beta 5$, $\alpha v\beta 6$," Cancer Res., (1994), 54: 2102-2107.

Gehlsen, K.R., et al., "Inhibition of In Vitro Tumor Cell Invasion by Arg-Gly-Asp-containing Synthetic Peptides," J. Cell. Biol. (1988) 106: 925-930.

Pierschbacher, M.D., et al., "Influence of Stereochemistry of the Sequence Arg-Gly-Asp-Xaa on Binding Specificity in Cell Adhesion," J. Biol. Chem., (1987) vol. 262, No. 36: 17294-17298.

Zhou, L.L., et al., "Adhesion of Human Trabecular Meshwork Cells to Extracellular Matrix Proteins," IOVS. (1996) vol. 37, No. 1: 104-113.

M.P. Lutolf, et al., "Synthetic matrix metalloproteinase-sensitive hydrogels for the conduction of tissue regeneration: Engineering cell-invasion characteristics," Proc. Nat. Acad. Sci. (2003) vol. 100, No. 9: 5413-5418.

M.P. Lutolf, et al., "Repair of bone defects using synthetic mimetics of collagenous extracellular matrices," Nature Biotechnol. (2003) vol. 21: 513-518).

M. Rafiuddin Ahmed, et al., "Peripheral nerve regeneration in RGD peptide incorporated collagen tubes," Brain Res. (2003) 993:208-216.

Oshitari, T, et al., "Effect of Chronic Hyperglycemia on Intraocular Pressure in Patients with Diabetes," Am. J. Ophthalmol. (2006) vol. 143 No. 2:363-365.

Mark S. Filla, et al., "In Vitro Localization of TIGR/MYOC in Trabecular Meshwork Extracellular Matrix and Binding to Fibronectin," Invest. Ophthalmol. Vis. Sci. (2002) vol. 43, No. 1:151-161.

Cheryl R. Hann, et al., "Ultrastructural Localization of Collagen IV, Fibronectin, and Laminin in the Trabecular Meshwork of Normal and Glaucomatous Eyes," Ophthalmic Res. (2001) 33: 314-324.

Cindy K. Bahler et al., "Pharmacologic Disruption of Schlemm's Canal Cells and Outflow Facility in Anterior Segments of Human Eyes," Invest. Ophthalmol. Vis. Sci. (2004) vol. 45, No. 7: 2246-2254.

Tezel, T.H. et al, "Posterior Vitreous Detachment with Dispase," Retina (1998) vol. 18: 7-15.

Curtis, T.M.et al., "Fibronectin attenuates increased endothelial monolayer permeability after RGD peptide, anti-$\alpha 5\beta 1$, or TNF-$\alpha$ exposure," Am. J. Physiol., (1995) 269: L248-L260.

Karmali, P. et al., Targeting of albumin-embedded paclitaxel nanoparticles to tumors; Nanomedicine, vol. 5, No. 1 (Mar. 1, 2009).

Arrowsmith, J. et al., Antitumor Imidazotetrazines. 41. Conjugation of the Antitumor Agents Mitozolomide and Temozolomide to Peptides and Leitropsins Bearing DNA Major and Minor Groove-Binding Structural Motifs; J. Med. Chem., vol. 45, pp. 5458-5470 (Dec. 5, 2002).

Lijie Men,et al., Further studies on the fragmentation of protonated ions of peptides containing aspartic acid, glutamic acid, cysteine sulfinic acid, and cysteine sulfonic acid; Rapid Communications in Mass Spectromotry, vol. 19, No. 1, pp. 23-30 (Jan. 15, 2005).

EP Supplemental Search Report dated Jun. 13, 2013 in related EP Application No. 10830687.9.

Atassi, M.Z. et al., "Enzymic and Immunochemical Properties of Lysozyme, XIII. Accurate Delineation of the Reactive Site Around the Disulfide 6-127 by Immunochemical Study of $\beta$-Propiolactone Lysozyme Derivative and of Synthetic Disulfide Peptides", Biochimica et Biophysica Acta, 420 (1976), pp. 358-375.

Office Action dated Nov. 11, 2014 in corresponding Japanese Patent Application No. 2012-538958.

Office Action dated Sep. 12, 2014 in corresponding Russian Patent Application No. 2012118503.

Barker, Peter L. et al.,"Antiplatelet and Antithrombotic Agents: From Viper Venom Proteins, to Peptides and Peptidomimetics, to Small Organic Molecules," Advances in Medicinal Chemistry, vol. 3, pp. 57-111. 1995.

Office Action dated Jan. 14, 2018 in related Israel Patent Application No. 229299.

* cited by examiner

PEPTIDES USEABLE FOR TREATMENT OF DISORDERS OF THE EYE

RELATED APPLICATION

This application is a continuation of copending U.S. patent application Ser. No. 15/867,101 filed on Jan. 10, 2018 and issuing on Jun. 4, 2019 as U.S. Pat. No. 10,307,460, which is a continuation of U.S. patent application Ser. No. 14/696,250 filed Apr. 24, 2015 and issued on Jan. 23, 2018 as U.S. Pat. No. 9,872,886, which is a continuation of U.S. patent application Ser. No. 12/943,900 filed Nov. 10, 2010 and issued on Apr. 28, 2015 as U.S. Pat. No. 9,018,352, which claims priority under 35 U.S.C. 119(e) to U.S. Provisional Patent Application Ser. No. 61/259,748 entitled Compositions And Methods For Inhibiting Cellular Adhesion To RGD Binding Sites filed on Nov. 10, 2009, the entire disclosure of each such patent and application being expressly incorporated herein by reference.

SEQUENCE LISTING

The instant application contains a Sequence Listing which has been submitted electronically in ASCII format and is hereby incorporated by reference in its entirety. Said ASCII copy created on Jul. 28, 2014 is named ALLEG-002A SL txt and is 4,969 bytes in size.

FIELD OF THE INVENTION

The present invention relates generally to the fields of chemistry and medicine and more particularly to compositions of matter and methods useable for inhibiting cellular adhesion to Arg-Gly-Asp (the "RGD" tripeptide) binding sites and related treatments for disorders such as inflammation, wound-healing, prevention of scar formation, thrombosis, cancer metastasis and tumors, proliferative or non-proliferative diabetic retinopathy, liquefaction of the vitreous humor, induction of posterior vitreo-retinal detachment (PVD), pathogenesis of vitreoretinal diseases, such as floaters, idiopathic macular hole, vitreomacular traction, age related macular degeneration, wet macular degeneration, choroidal neovascularization, vitreoretinal surgery, vein occlusion, corneal neovascularization, ischemic optic nerve, rubiosis iridis and prevention of scar formation in glaucoma surgery.

BACKGROUND OF THE INVENTION

The RGD tripeptide sequence is found in a number of proteins, where it plays a role in cell adhesion. Examples of proteins in which the RGD tripeptide sequence is present include collagens, fibronectin, vitronectin, von Willebrand factor (VWF), certain disintegrins, and certain discoidins.

Integrins are heterodimeric cell surface receptors which mediate adhesion between cells and the extracellular matrix (ECM) by binding to ligands having an exposed RGD sequence. Normal integrin-RGD binding is believed to play a role in gene expression involved in cell growth, migration, and survival. Faulty regulation of such cell growth, migration, and survival can result in a number of disease states including thrombosis, inflammation, and cancer. Thus, RGD peptides have been investigated as potential mimics of cell adhesion proteins and for their ability to bind to integrins, for therapeutic purposes such as inhibiting apoptosis, angiogenesis, tumorigenesis, for the use in their multimeric form as internal radiotherapeutic agents as well as cancer imaging agents and for their anti-cancer drug carrying abilities.

In the eye, integrins affect a number of processes including ocular development, cell migration, healing and some pathologic processes. Integrins may also modulate inflammation and thrombosis in ocular tissue. Intravitreally injected RGD peptide has also been reported to cause posterior vitreoretinal detachment in an animal model and, thus, may be useful in the treatment of certain retinal disorders and/or to facilitate removal of the vitreous body in a vitrectomy procedure. [See Olivera, L. B., et al., *RGD Peptide—Assisted Vitrectomy to Facilitate Induction of a Posterior Vitreous Detachment: a New Principle in Pharmacological Vitreolysis*; Current Eye Research (8):333-40 (Dec. 25, 2002)].

SUMMARY OF THE INVENTION

The present invention provides novel compounds comprising R-G-Cysteic Acid (i.e., R-G-NH—CH($CH_2$—$SO_3H$)COOH or Arg-Gly-NH—CH($CH_2$—$SO_3H$)COOH) and derivatives thereof (including pharmaceutically acceptable salts, hydrates, stereoisomers, multimers, cyclic forms, linear forms, drug-conjugates, pro-drugs and their derivatives).

The present invention also provides compositions and methods for inhibiting cellular adhesion to RGD binding sites or delivering other diagnostic or therapeutic agents to RGD binding sites in human or animal subjects by administering to the subject an effective amount of a composition comprising an R-G-Cysteic Acid peptide or a derivative thereof (including pharmaceutically acceptable salts, hydrates, stereoisomers, multimers, cyclic forms, linear forms, drug-conjugates, pro-drugs and their derivatives). Specific examples of R-G-Cysteic Acid peptide of this invention include a linear form of Arg-Gly-NH—CH($CH_2$—$SO_3H$)COOH (example referred to herein as Compound 1) and a cyclic form of Arg-Gly-NH—CH($CH_2$—$SO_3H$)COOH) (example referred to herein as Compound 2).

General formulas for R-G-Cysteic Acid derivatives of the present invention include but are not limited to compounds having General Formulas I-VII as follows:

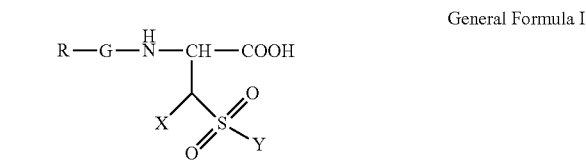

General Formula I where X is selected from: H, $C_1$-$C_6$ alkyl, Ph or $SO_3H$ and Y=OH or $NH_2$.

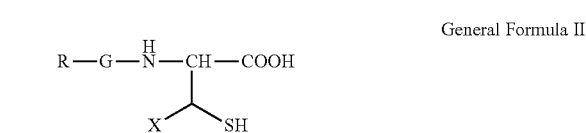

General Formula II where X is selected from: H, $C_1$-$C_6$ alkyl, Ph or $SO_3H$.

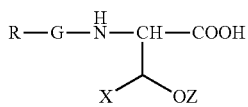

General Formula III where X is selected from: H, $C_1$-$C_6$ alkyl, Ph or $SO_3H$ and wherein Z is selected from: H or $SO_3H$

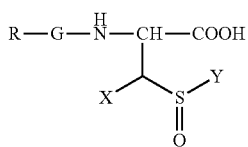

General Formula IV where X is selected from: H, $C_1$-$C_6$ alkyl, Ph or $SO_3H$; Y is selected from OH or $NH_2$.

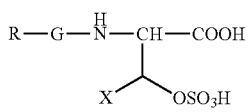

General Formula V where X is selected from: H, $C_1$-$C_6$ alkyl, Ph or $SO_3H$.

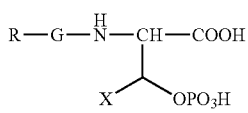

General Formula VI where X is selected from: H. $C_1$-$C_6$ alkyl, Ph or $SO_3H$.
General Formula VII:

$X_1$—R-G-Cysteic Acid-X where X and $X_1$ are selected from: cyclic or linear -Phe-Val-Ala, -Phe-Leu-Ala, -Phe-Val-Gly, -Phe-Leu-Gly, -Phe-Pro-Gly, -Phe-Pro-Ala, -Phe-Val, or any salt of any combination of the D-isomer or L-isomer of: Arg, Gly, Cysteic, Phe, Val, Ala, Leu, Pro, Thr.

Examples of cyclic forms of General Formula VII include but are not necessarily limited to (SEQ ID NO: 1):

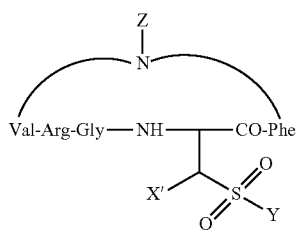

where X' is selected from: H, $C_1$-$C_6$ alkyl, Ph or $SO_3H$ and Z is selected from H or Me; Y is selected from OH, $NH_2$.

Sulfonic acids are stronger acids than corresponding carboxylic acids. This higher polarity of the sulfonic acid group leads to stronger intermolecular bonding. For example, R-G-Cysteic acid, which has a more polarized O—H bond, may form stronger hydrogen bonds than R-G-Aspartic acid (RGD peptide), which has a relatively less polarized O—H bond, with the amide groups of the proteins in the integrin binding site and/or have stronger interactions with metal ions complexed in the integrin binding site.

As described in more detail elsewhere herein, one specific example of General Formula VII, Glycinyl-Arginyl-Glycinyl-Cysteic(Acid)-Threonyl-Proline-COOH (GRG Cysteic Acid TP; referred to below as Compound 1) (SEQ ID NO: 2) was synthesized and tested in animals and found to be effective in inducing posterior vitreous detachment (PVD) from retina surface by inhibiting integrin-extracellular matrix (ECM) interactions. As described also in more detail elsewhere herein, Compound 1 was tested in a model of wound healing using human umbilical vein endothelial cells (HUVEC) and was shown to inhibit cell adhesion by 74% in 12 hours compared to an inhibition of 40% by a cyclic-RGD peptide. These studies suggest and corroborate the rationale that Glycinyl-Arginyl-Glycinyl-Cysteic(Acid)-Threonyl-Proline-COOH (SEQ ID NO: 2) may bind to integrin even more strongly than RGD peptides themselves.

The RGCysteic Acid peptide sequence, which can be in either L-form or D-form, is a competitive inhibitor of integrin-ECM interactions. The RGCysteic Acid peptide sequence can be of protease-resistant derivatives or of cyclic derivatives or of pro-drug derivatives or associated with drug delivery systems or of monoclonal antibodies.

The compositions of the present invention are useable to inhibit angiogenesis, which can be useful for treating inflammation, wound-healing, thrombosis, cancer metastases and tumors. Further useful application can be found in ophthalmology including, proliferative or non-proliferative diabetic retinopathy, liquefaction of the vitreous, induction of posterior vitreo-retinal detachment (PVD), pathogenesis of vitreoretinal diseases, such as idiopathic macular hole, vitreomacular traction, age related macular degeneration, wet macular degeneration, choroidal neovascularization, vitreoretinal surgery, vein occlusion, and prevention of scar formation in glaucoma surgery. Still further, multimeric and/or radiolabeled compositions of the present invention are useable as diagnostic/imaging agents for the detection of tumors and radiotherapeutic agents for the treatment of tumors and as anti-cancer drug carriers due to their tumor directing properties.

Biomaterials incorporating an R-G-Cysteic Acid peptide can also provide a synthetic adhesive microenvironment for the long term survival and growth of cells and for the engineering of living tissues for applications in tissue engineering and regenerative medicine. Through their property of binding integrin adhesion receptors, R-G-Cysteic Acid peptides can provide an adhesion-promoting signal when it is tethered onto a biomaterial or scaffold. R-G-Cysteic Acid-based materials mediate cell adhesion, spreading, and migration of cells. In addition, integrin-mediated cell adhesion promotes cell proliferation and survival and plays a key role in assembly and organization of multicellular structures and tissues.

Drugs for the treatment of macular degeneration like Lucentis and Avastin are based on inhibiting VEGF, which otherwise causes the growth of new vessels, angiogenesis, and consequently contributes macular edema. It has been known that a small peptide RGD can induce apoptosis by inhibiting cell attachment to extracellular matrix[1] by competitive binding as shown in U.S. Pat. No. 6,500,924 to Brooks et al.

The RGD peptide binding or recognition motif can be found in the proteins of extracellular matrix and integrins which link the intracellular cytoskeleton of cells with the ECM by recognizing the RGD adhesion epitopes. See, for example, Foos, R Y., Invest. Opthalmol. Vis. Sci. (1972) 11, 801-808. Cells, without the attachment to the ECM, normally undergo apoptosis.

In general, interactions between fibroblasts and glycoprotein components of extracellular matrix cause a major scar formation mediated primarily by the RGD containing amino acid sequence interacting on the cell surface integrins. It has also been known that the RGD sequence is involved in cell-ECM interactions during inflammatory and homeostatic reactions (see Hershkoviz, S. M., et al., Invest. Ophthalmol. Vis. Sci., (1994), 35, 2585-2591) and the integrins play an important role in cell migration in wound healing or pathologic processes and modulating inflammation and thrombosis. Thus, potent integrin antagonists, like RGD peptides, might be very useful as pharmacologic agent as anti-inflammatory, anti-metastatic or anti-thrombotic agents (see Elner, S. G. and Elner, V. M., IOVS (1996) 37:696-701. It is also reported in literature that CD44 receptor for hyaluronic acid mediates cell-cell and cell-matrix interactions through its affinity for hyaluronic acid, and possibly also through its affinity for other ligands such as osteopontin, collagens, and matrix metalloproteases (MMPs).

Adhesion with hyaluronan plays an important role in cell migration, tumor growth and progression and also involved in lymphocyte activation, recirculation and homing, and hematopoiesis. Altered expression or dysfunction causes numerous pathogenic phenotypes (see for example, Jiang D., Annu. Rev. Cell. Dev. Biol. (2007) 23: 435-461; and Knudson, W. et al, Matrix Bio. (2002), 21: 15-23).

Recently, it has been shown that the interaction of CD44 and cell-matrix components (e.g., HA) plays a significant role in the development of various inflammatory diseases and interruption of hyaluronan-CD44 interactions would lead to amelioration of choroidal neovascularization (see Hiroshi Mochimaru et al., Invest. Ophthalmol. Vis. Sci. (2009) 50: 4410-4415).

These evidences demonstrate that an adhesion molecule like RGD peptide or CD44 in cell-cell and cell-ECM interactions plays an important role in the development of numerous pathogenic diseases and the inhibition of the interactions can be a novel therapeutic target in treating and curing the diseases.

Synthetic peptides have also been shown to bind to integrins and growth factors. Cyclized pentapeptides containing RGD sequences have been found to inhibit binding of vitronectin to $\alpha_v\beta_3$ integrin (see Michael A. Dechantsreiter, et al., J. Med. Chem. (1999) 42:3033-3040) and both vitronectin and fibronectin to $\alpha_v\beta_3$ and $\alpha_{IIb}\beta_3$ integrins (see Roland Haubner et al., J. Am. Chem. Soc., (1996) 118:7461-7472). This inhibition has been shown to be useful in the treatment of multiple, unrelated diseases. In hamster studies, the cyclic pentapeptides delayed growth and metathesis of tumors in comparison with control animals (see M. A. Buerkle et al., British J. Cancer (2002) 86: 788-795). The pentapeptides have also been shown to reduce binding of sickle red blood cells to vascular endothelium and improved hemodynamic behavior (see Eileen M. Finnegan et al., Am. J. Physiol. Heart Circ. Physiol., (2007) 293: H1038-H1045). Another cyclic peptide containing the RGD sequence has shown strong binding to $\alpha4\beta1$, an integrin known to play a role in leucocyte binding in inflammatory and immune responses (see Pina M. Cardarelli et al., J. Biol. Chem. (1994) 269:18668-18673). A synthetic, sulfated tetrapeptide has been shown to strongly bind to VEGF (see Maynard, J. A. Hubbell, Acta Biomaterialia (2005) 1: 451-459).

In addition, in an important and useful application, a dimeric RGD peptide-drug conjugate has been shown to be useful for integrin-targeted drug delivery for tumor targeting (see Chen et al., J. Med. Chem., (2005) 48(4): 1098-1106).

In another equally important and useful application, multimeric radiolabeled RGD peptides have been shown to be useful as diagnostic/imaging agents for tumor detection and, as radiotherapeutic agents for tumor specific targeting and treatment by targeting the integrin $\alpha_v\beta_3$ (see Zi-Bo Li et al., J. Nucl. Medicine, (2007) 48: 1162-1171).

In ophthalmology, scar formation in wound healing by fibroblast is one of the major problems, particularly in glaucoma. This arises from interactions between fibroblast and glycoprotein components of ECM. Recognition of ECM glycoproteins occurs via cell surface integrins that are specific for adhesion epitopes, such as the Arg-Gly-Asp (or RGD) sequence. The RGD sequence, which is present in several matrices of plasma proteins, including fibronectin (FN) and vitronectin (VN), is involved in cell-ECM interactions that occur during inflammatory and homeostatic reactions. Inhibition of the interactions between fibroblast and glycoproteins of ECM alleviated the scar formation (see Rami Hershkoviz et al., Invest. Ophthalmol. Vis. Sci. (1994) 35: 2585-2591).

The collagen fibrils of the posterior vitreous cortex adhere to the vitreoretinal interface, specifically to the inner limiting lamina of the retina surface (see Sebag J., Eye (1992), 6: 541-552). The adherence at the vitreous base, the optic disc, along the major retinal vessels and in a facial manner to the entire posterior pole plays an important role in the pathogenesis of vitreoretinal diseases, such as idiopathic macular hole, vitreomacular traction, proliferative diabetic retinopathy, etc. (Akiba J. Quiroz M. A., et al., Ophthalmol. (1990) 97, 1619-1655).

Angiogenesis inhibition is showing early promise with diabetic retinopathy and macular degeneration, which both result from an overgrowth of ocular blood vessels. In these disorders, the vessels interfere with normal structures in the eye, or they block light from reaching the back of the eye. The new blood vessels are themselves the primary pathology, and stopping blood vessel growth could prevent blindness. Thus, angioinhibition could result in not just a treatment of these disorders; it could be a cure. Furthermore, it has been postulated that separation of the vitreous from the retina can alleviate macular traction, reducing the risk of macular hole formation. Accordingly, the posterior vitreous detachment by the inhibition of fibronectin and laminin binding to the integrins on the vitreoretinal interface, may prevent retinal neovascularization in eyes with diabetic retinopathy and retinal vein occlusion (see Akiba J. Quiroz M A, Ophthalmol. (1990) 97, 1619-1655; Kelly N. E., et al., Arch. Ophthalmol. (1991) 109, 654-659; and Kado M, et al., Am. J. Ophthalmol. (1988) 105: 20-24).

In recent years, vitreous surgical procedures have been greatly improved to relieve vitreoretinal tractions and to reduce retinal edema. Despite continued improvement in surgical techniques and instrumentation, it still remains difficult to achieve an atraumatic removal of the vitreous cortex in some patients particularly in diabetic retinophathy and pediatric patients due to complications such as retinal breaks, retinal detachment and retinal nerve fiber damage (see Sebag J., Arch. Clin. Exp. Ophthalmol. (1987) 225: 89-93; and Han D. P., et al., Arch. Ophthalmol. (1998) 106: 998-1000) etc. Thus, a less traumatic approach to selectively cleave the vitreous interface without damaging the retina is highly desirable. In recent years, reports concerning a number of pharmacologic agents for the separation of the vitreoretinal interface have appeared in literature (see Trese M. T., Eye. (2002) 16: 365-368; Gandorfer A., et al., Am. J. Ophthalmol. (2002) 133: 156-159; and Hesse L., et al., Eye Res. (2000) 70: 31-39). The pharmacologic vitreolysis using enzymes such as hyaluronidase (see U.S. Pat. No. 6,863,886 to Karageozian et al.) and autologous plasmin (Sakuma T, et al., Nippon Ganka Gakkai Zassi (2003) 107: 709-718) have been explored to promote the digestion of extracellular matrix and to induce posterior vitreous detachment in the past. Yet, a non-specific destruction of adjacent tissues by the enzymes employed impedes success of their therapeutic application. In the last few years, a novel approach using non-enzymatic pharmacologic agents like urea (see Nickerson, C., et al., in J. Biomechanics, (2008) 41: 1840-1846, and in Macromol. Symp. (2005): 183-189) and RGD peptide (see Leonardo B. Oliviera, et al., Curr. Eye Res. (2002) 25: 333-340) has been investigated by concentrating on the separation of vitreoretinal interface. It has been shown that a synthetic analog of RGD peptide competes for the RGD motif of ECM proteins to disrupt integrin-ECM interactions and to loosen the attachments in-vitro (Williams J. A., Pathol. Bio. (1992) 40: 813-821; Gehlsen K. R., et al., J. Cell. Biol. (1988) 106: 925-930; Pierschbacher, M. D., et al., J. Biol. CHem., (1987) 262: 17294-17298; and Zhon L. L., et al., IOVS. (1996) 37: 104-113) and in-vivo. Thus, the intravitreal injection of soluble RGD peptides led to a release of RGD-epitopes from the insoluble ECM proteins of the retinal surface, consequently facilitating the non-enzymatic PVD in rabbit models. Clearly, these results indicate that the vitreoretinal interface involves integrin connection to RGD motif of ECM as well as adhesion of vitreous cortical collagens to the inner limiting lamella (ILL). RGD peptides and their derivatives promote migration of epithelial cells in a wound (see P. M. Mertz et al., J. Burn Care Res. (1996) 17: 199-206) and maintain their bioactivity when incorporated into synthetic biomaterials such as hydrogels (see M P Lutolf, et al., Proc. Nat. Acad. Sci. (2003) 100: 5413-5418; and M P Lutolf, et al., Nature Biotechnol. (2003) 21: 513-518), other polymer matrices (see Horng-Ban Lin et al., J. Biomed. Material. Res. (2004) 28: 329-342) or as surface films on hard substrates (D. M. Ferris et al., Biomaterials (1999) 20: 2323-2331). RGD peptides also promote increased adhesion of epithelial or endothelial cells to vascular prostheses (see K. Walluscheck el al., Eur. J. Vascular and Endovascular Surgery (1996) 12: 321-330) and other artificial organs (see Jeschke, Brigette, Biomaterials (2002) 23: 3455-3463) coated with the peptide sequence and have been shown to support nerve regrowth (see M. Rafiuddin Ahmed et al., Brain Res. (2003) 993:208-216). The prostheses's biologically active surface can contain synthetic resin fibers or polymers.

DETAILED DESCRIPTION AND EXAMPLES

Figure 1:
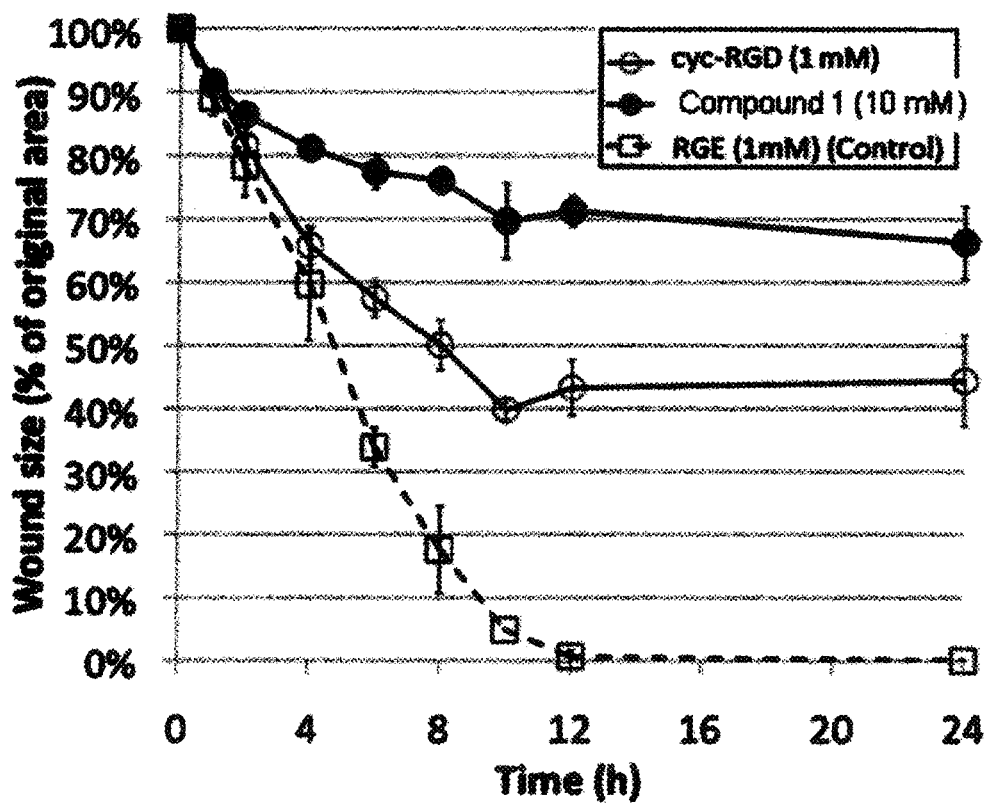
FIG. 1 shows the effect of three peptides, namely, cyclic-RGD-peptide, RGCysteic acid peptide (Compound 1) (SEQ ID NO: 2) and RGE peptide, on the kinetics of wound healing.

The present invention provides novel compounds, including those of General Formulas I through VII above. Specific examples include linear form of Arg-Gly-NH—CH(CH$_2$—SO$_3$H)COOH (example referred to herein as Compound 1)(SEQ ID NO: 2) and cyclic form of Arg-Gly-NH—CH (CH$_2$—SO$_3$H)COOH) (example referred to herein as Compound 2) (SEQ ID NO: 1) as well as derivatives thereof, including pharmaceutically acceptable salts, hydrates, stereoisomers, mutimers, cyclic forms, linear forms, multimeric forms, drug conjugates, pro-drugs and their derivatives.

Synthesis of Compounds 1 and 2

Conventional solid-phase peptide synthesis (SPPS; see R. B. Merrifield, *J. Am. Chem. Soc.* (1963) 85 (14): 2149-2154) known to a person of ordinary skill in the art maybe carried out. The SPPS is a preferred method of synthesis because of the high yields. In general, the first stage of the solid phase peptide synthesis technique consists of peptide chain assembly with protected amino acid derivatives on a polymeric support. The second stage of the technique is the cleavage of the peptide from the resin support with the concurrent cleavage of all side chain protecting groups to give the crude free peptide. The general principle of SPPS is one of repeated cycles of coupling-deprotection. The free N-terminal amine of a solid-phase attached peptide is coupled to a single N-protected amino acid unit. This unit is then deprotected, revealing a new N-terminal amine to which a further amino acid may be attached. See Asymmetric Synthesis by Von G. M. Coppola and H. F. Schuster; John Wiley & Sons, New York 1987 for synthesis, protection and deprotection strategies and Greene's Protective Groups in Organic Synthesis by Peter G. M. Wuts and Theodora W. Greene, (2nd edition) J. Wiley & Sons, 1991. for protection and deprotection strategies.

Of the two major used forms of solid phase peptide synthesis—Fmoc (9-fluorenylmethyloxycarbonyl; base labile alpha-amino protecting group) and t-Boc (t-butyloxycarbonyl; acid labile protecting group), Fmoc may be used preferably in the synthesis of the present peptides. Each method involves different resins and amino acid side-chain protection and consequent cleavage/deprotection steps. After cleavage from the resin, peptides are usually purified by reverse phase HPLC using columns such as C-18, C-8, and C-4.

An Example of Solid Phase Peptide Synthesis

The following is an outline of the synthetic steps for peptide synthesis on Wang resin as the solid support, using the base labile 9-fluorenylmethyloxycarbonyl (Fmoc) protecting group.

Fmoc Deprotection

Load 0.08 mmol of Fmoc-Pro-Wang resin into a fritted column equipped with a plastic cap. Wash the resin with 2×3-ml portions of DMF (dimethylformamide) for 1 minute each. Next, add about 3 ml of 20% piperidine in DMF and allow the Fmoc deprotection to continue for 15 minutes. During this time, gently swirl or agitate the column to assure a complete mixing. After the reaction is complete (about 15 min.), drain the reaction column and wash the resin again with DMF (4×3 ml).

Amide Bond Coupling

The desired Fmoc-protected amino acid, Fmoc-Thr-tBu, (3 eq.; relative to resin loading indicated by supplier) and DIEA (6 eq.) in DCM (0.5 M with respect to the amino acid) are then added to the resin. The mixture is cooled at −20° C. for 20 minutes. Next, benzotriazol-1-yl-oxytripyrrolidinophosphonium hexafluorophosphate (PyBOP), a peptide coupling reagent used in solid phase peptide synthesis (3 eq.) is added to the reaction. After shaking at −20° C. for 8 hours, the reaction mixture is drained and the resin is washed with DCM (3×).

After the Fmoc deprotection using 20% piperdine in DMF (15 min) and the wash with DMF (3×), the next Fmoc protected amino acid (3 eq.; relative to resin loading), PyBop (is coupled in the same manner as above.

Cleavage

In order obtain the peptide in the free acid form, the ester linkage is cleaved using strongly acidic conditions such as TFA (trifluoroacetic acid). Treat the resin with 2-3 ml of a solution of trifluoroacetic acid and water 95:5. Gently agitate the resin over a period of 25 minutes. Next, drain the column and carefully collect the filtrate into a glass collection vessel.

Synthesis of Compound 1 (GRG Cysteic Acid TP)(SEQ ID NO: 2):

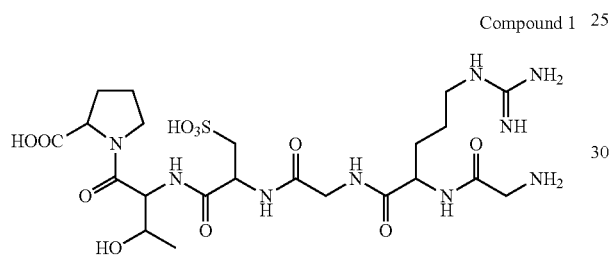

Compound 1

Step 1. Resin Loading: An o-chlorotrityl resin preloaded with proline is used as the starting material.

Step 2. Peptide assembly: Fmoc synthesis is used to assemble the peptide. Protected amino acids are activated with PyBOP and the terminal Fmoc groups removed with 20% piperidine in DMF. The following protected amino acids are used in the order in the order in which they appear:
 a. Fmoc-Thr-tBu (Fmoc threonine-t-butyl ester)
 b. Fmoc-cysteic acid-Pfp (Fmoc cysteic acid-pentafluorophenyl ester)
 c. Fmoc-Gly (Fmoc glycine)
 d. Fmoc-Arg-Pbf (N$_\alpha$-Fmoc-Nω-(2,2,4,6,7 pentamethyl-dihydrobenzofuran-5-sulfonyl)-L-arginine)
 e. Fmoc-Gly (Fmoc glycine)

Step 3. Peptide cleavage from Resin: The resulting peptide is cleaved from the solid support and the protecting groups removed with a solution of 85.5% TFA, 5% phenol, 2% water, 5% thioanisole, and 2.5% ethanedithiol.

Step 4. Purification: High Performance Liquid Chromatography (HPLC), is used to purify the resulting RGC peptides.

Figure 2:
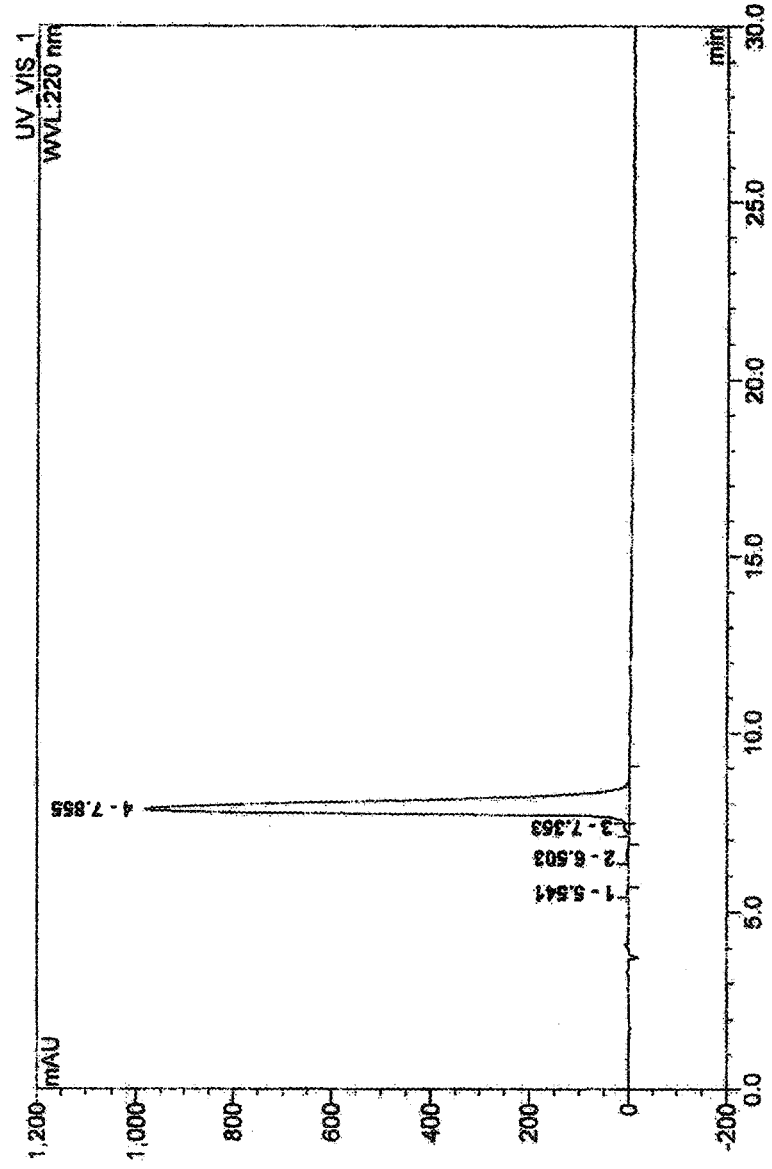
FIG. 2 shows and HPLC chromatogram of R-G-Cysteic acid peptide (Compound 1) (SEQ ID NO: 2)
Figure 3:
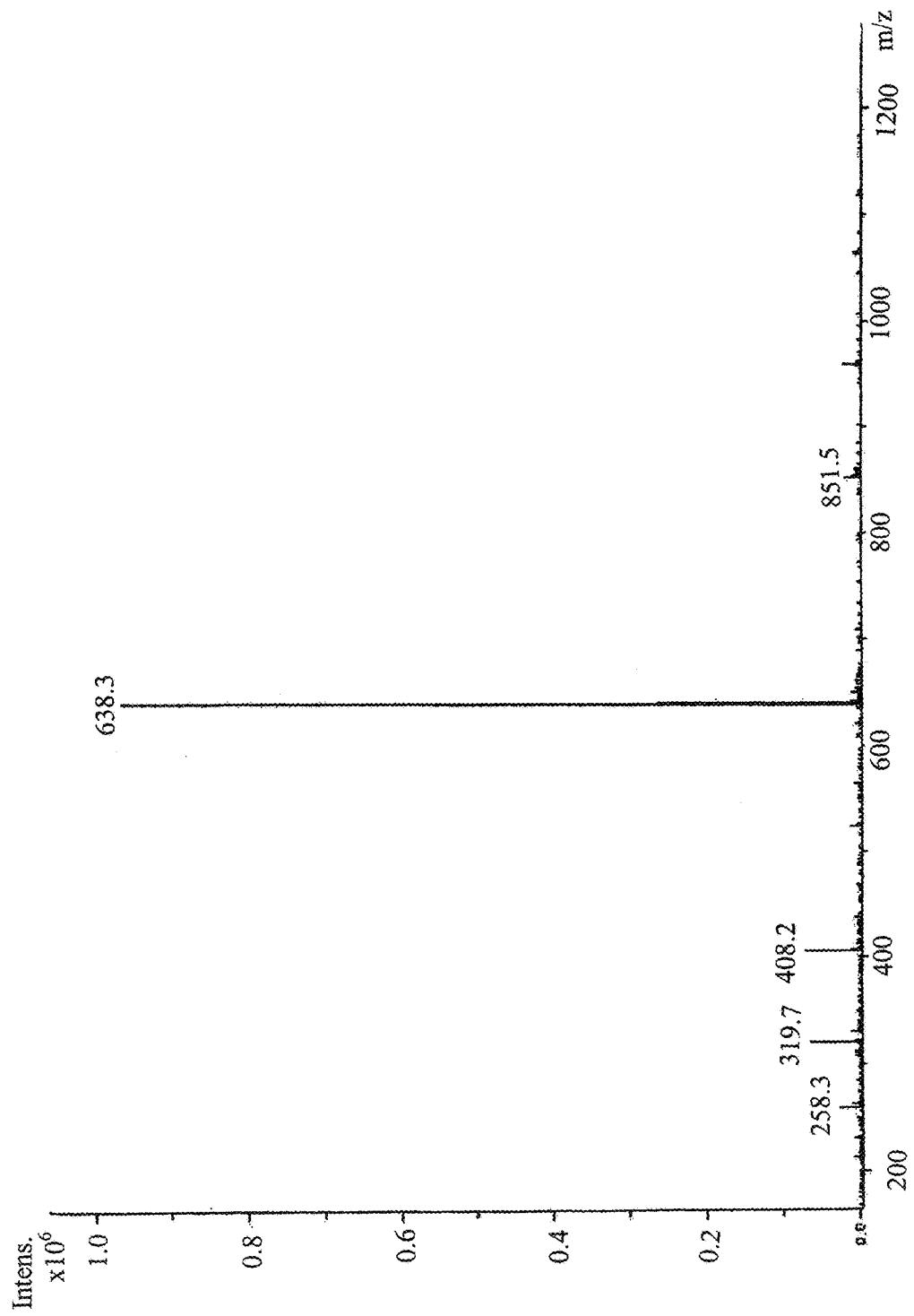
FIG. 3 shows an Electrospray mass chromatogram of R-G-Cysteic acid peptide (Compound 1) (SEQ ID NO: 2)

A quantity of Compound 1, prepared as described above, was analyzed by High Performance Liquid Chromatography to be >98% area/area in purity [HPLC conditions: Buffer A: 0.1% trifluoroacetic acid (TFA) in water, Buffer B: 0.1% TFA in acetonitrile, Mobile Phase (MP) A: 97% Buffer A and 3% Buffer B, Mobile Phase B: 79% Buffer A and 21% Buffer B, Mobile Phase C: 50% Buffer A and 50% Buffer B; for gradient see Table 1 below; flow rate: 1.0 mU/minute; column: Waters Symmetry@ C18, 5µ, 4.6×250 mm; column temperature: 30° C.; detector: UV@220 nm; sample injection volume: 20.0 µL; sample preparation: 20 µL sample diluted with 1.0 mL Mobile Phase A (approximately 0.5 mg/mL)]. The corresponding HPLC chromatogram is shown in FIG. 2. In addition, based on the stepwise addition of the corresponding amino acids for the synthesis of the peptide sequence, the molecular weight of purified Compound 1 was determined by Electrospray Mass Spectrometry to be 638.3 amu (theoretical mass: 637.7 amu), confirming the identity of Compound 1. The Electrospray mass spectrogram of Compound 1 is shown in FIG. 3.

TABLE 1

Pump Gradient Program to detect Compound 1 by HPLC
Pump Gradient Program

| Step | Time | % MP A | % MP B | % MP C |
| --- | --- | --- | --- | --- |
| 0 | 0.1 min | 100 | 0 | 0 |
| 1 | 60 min | 0 | 100 | 0 |
| 2 | 20 min | 0 | 0 | 100 |
| 3 | 15 min | 100 | 0 | 0 |

Synthesis of Compound 2 (Cyclo-RGCysteic Acid fN(CH$_3$)V) (SEQ ID NO: 1):

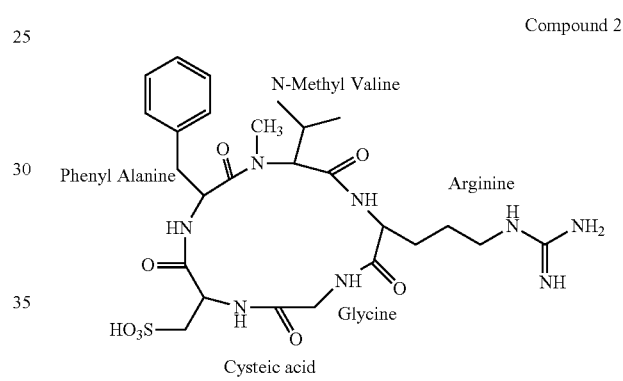

Compound 2

Step 1. Loading Resin: An o-chlorotrityl resin is used as the starting material. Fmoc-N☐-methyl-L-Val is attached to the resin.

Step 2. Peptide Assembly: 2. Fmoc synthesis is used for the peptide assembly. Protected amino acids are activated with PyBOP and the terminal Fmoc groups removed with 20% piperidine in DMF. The following protected amino acids are used in the order in which they appear:
 a. Fmoc-Phe (Fmoc-phenyl alanine)
 b. Fmoc-cysteic acid-PfP (Fmoc-cysteic acid pentafluorophenyl ester)
 c. Fmoc-Gly (Fmoc-glycine)
 d. Fmoc-Arg-Pbf (N$_\alpha$-Fmoc-Nω-(2,2,4,6,7 pentamethyl-dihydrobenzofuran-5-sulfonyl)-L-arginine)

Step 3. Peptide cleavage from resin: The peptide is cleaved from the solid support using acetic acid/TFA/DCM (1:3:3)

Step 4. Cyclization and deprotection to desired cyclic peptide: Cyclization via in situ activation using diphenylphosphorylazide and sodium bicarbonate under high dilution. The side chains are deprotected using 85.5% TFA, 5% phenol, 2% water, 5% thioanisole, 2.5% ethanedithiol.

Step 5. Purification: HPLC is used for purification.

Figure 4:
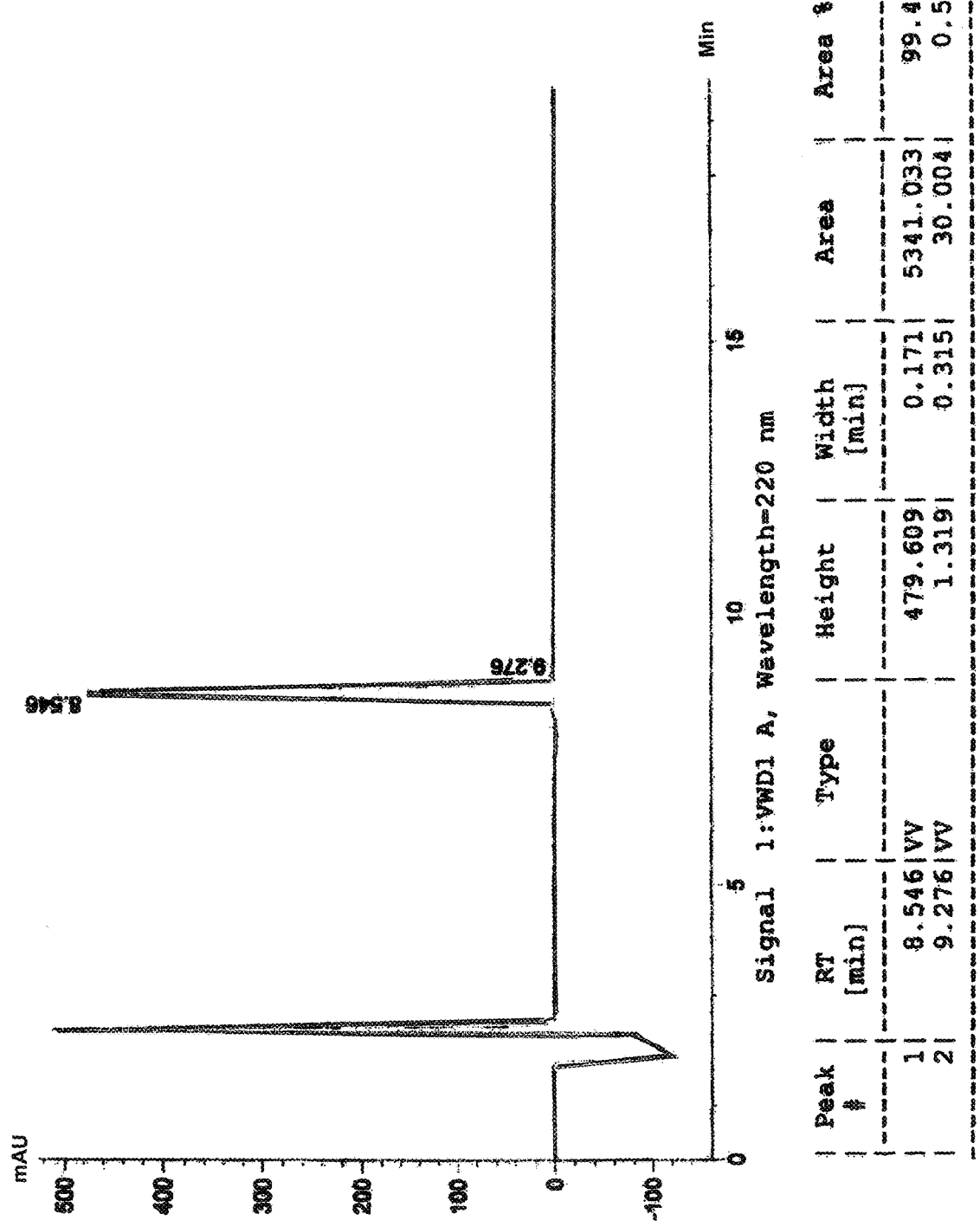
FIG. 4 shows and HPLC chromatogram of cyclic R-G-Cysteic acid peptide (Compound 2) (SEQ ID NO: 1)
Figure 5:
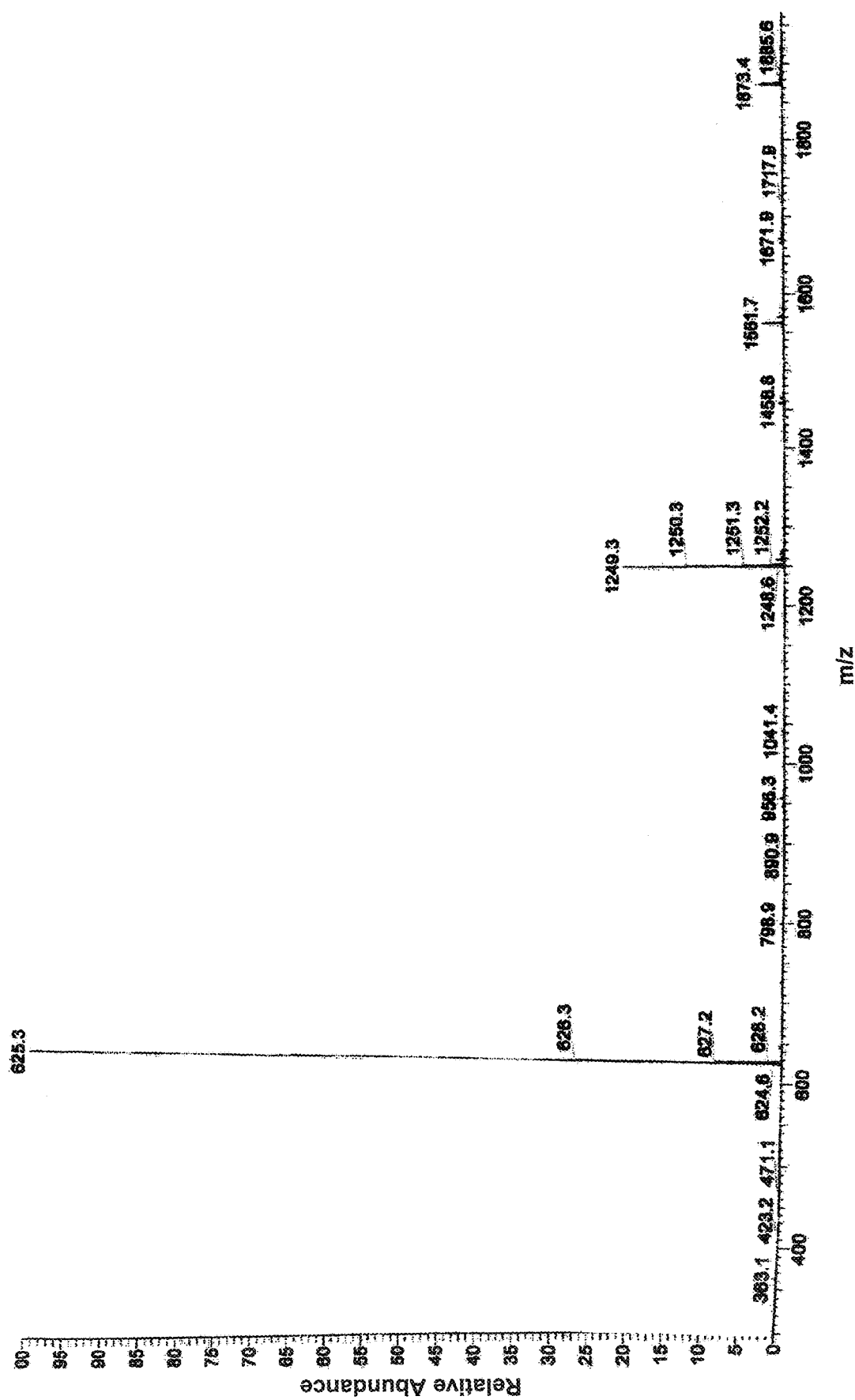
FIG. 5 shows an Electrospray mass chromatogram of cyclic R-G-Cysteic acid peptide (Compound 2) (SEQ ID NO: 1).

A quantity of Compound 2, prepared as described above was analyzed by High Performance Liquid Chromatography to be >99% area/area in purity (HPLC conditions: Mobile Phase A: 0.1% trifluoroacetic acid in water, B: 0.1% TFA in (80% acetonitrile plus 20% water); gradient 26% to 36% B in 20 minutes; flow rate: 1.0 mL/minute; column: Phenomenex C18(2) 4.6×150 mm, 5μ, 100 A; detector: UV@220 nm; sample injection volume: 100.0 μL). The corresponding HPLC chromatogram is shown in FIG. 4. In addition, based on the stepwise addition of the corresponding amino acids for the synthesis of the peptide sequence, the molecular weight of purified Compound 2 was determined by Electrospray Mass Spectrometry to be 625.3 amu (theoretical mass: 625.77 amu), confirming the identity of Compound 2. The Electrospray mass spectrogram of Compound 2 is shown in FIG. 5.

Methods for Inhibiting Cellular Adhesion

The present invention also provides methods for inhibiting cellular adhesion to RGD binding sites in a human or animal subject by administering to the subject an effective amount of R-G-Cysteic Acid (i.e., linear form of R-G-NH—CH($CH_2$—$SO_3H$)COOH or cyclic form of R-G-NH—CH($CH_2$—$SO_3H$)COOH) or a derivative thereof (including pharmaceutically acceptable salts, hydrates, stereoisomers, multimers, cyclic forms, linear forms, drug-conjugates, prodrugs and their derivatives).

Applicant has discovered that synthetic RGCysteic Acid peptides of the present invention induce apoptosis by competitively inhibiting the cell attachment to the ECM components. Therefore, the present synthetic RGCysteic acid peptides and their derivatives can be used as potent integrin antagonists as therapeutic agent against angiogenesis, inflammation, cancer metastasis, thrombosis, prevention and treatment of scar formation as well as a pharmacological vitreolysis agents. In addition, in an important aspect of the present invention, an improved targeting of the α, β integrins using multimerized and radiolabeled RGC peptides, for use as internal radiotherapeutic agents for tumor detection (diagnostic or imaging agent) and tumor treatment is envisaged. In another important aspect, improved RGC peptide conjugates or multimeric RGC peptide conjugates function as drug carriers, for example, as anti-cancer drug carriers for efficient tumor targeting.

As described elsewhere herein, the sulfonic acids in the RGC-peptides are stronger acids than corresponding carboxylic acids in RDG-peptides. This higher polarity of the sulfonic acid group leads to stronger intermolecular bonding. For example, R-G-Cysteic acid, which has a more polarized O—H bond, may form stronger hydrogen bonds than R-G-Aspartic acid, which has a relatively less polarized O—H bond, with the amide groups and/or side chains of the amino acids of the proteins in the integrin binding site and/or have stronger interactions with metal ions complexed in the integrin binding site. Therefore, the novel R-G-Cysteic acid peptides and their derivatives of the present invention present improved compounds and compositions over the corresponding RGD peptides in integrin receptor recognition and binding.

Additionally, in diabetic patients with chronic hyperglycemia associated with elevated IOP, open angle glaucoma particularly is reported to be related to the accumulation of fibronectin in the trabecular meshwork tissue and the excess of fibronectin is believed to inhibit the aqueous outflow (see Oshitari, T, et al., Am. J. Ophthalmol. (2007) 143:363-365). Involvement of fibronectin in the cell-ECM interaction in the trabecular meshwork was indicated in primary open angle glaucoma (see Mark S. Filla, et al., Invest. Ophthalmol. Vis. Sci. (2002) 43:151-161; and Cheryl R. Hann, et al., Ophthalmic Res. (2001) 33: 314-324). It has also been reported that the endothelial cells of Schlemm's canal interact with extracellular matrix in influencing outflow facility (see Cindy K. Bahler et al., Invest. Ophthalmol. Vis. Sci. (2004) 45: 2246-2254). In light of the inhibition of the aqueous outflow by the presence of an excess of extracellular matrix components such as fibronectin, application of RGCysteic acid peptides and their derivatives to treat the elevated IOP of diabetic patients would be highly beneficial to diabetic patients.

The preferred RGCysteic acid peptides can be a fusion polypeptide, a cyclic or linear polypeptide, a derivatized polypeptide, including RGCysteic acid peptide derivatized or associated or coupled with drug delivery systems or other drugs, such as, for example, anti-cancer drugs, a multimerized RGC peptide, a monoclonal antibody containing RGCysteic acid sequence that immunoreacts with integrins' binding site or functional fragment thereof.

RGCysteic acid containing polypeptides can have a sequence corresponding to the amino acid residue sequence of natural integrin adhesive binding region, such as those present in fibrinogen, fibronectin, vitronectin, von Willebrand factor, laminin, thrombospondin, and the like ligands.

The present peptide sequence consists of three amino acids having terminal guanidino, sulphonic and carboxylic groups and its derivatives coupled and/or associated with drug delivery systems, including peptide fragments, glycoproteins, and polymer groups such as PEG, Pluronic, and other polymer groups, and, liposomes and nanoparticles. Pharmaceutical compositions comprising them for treatment of various pathological disorders include injectable, gel, suspension, ointment, solid and liquid dosage forms.

Integrin receptors associated with a cell adhesion motif such as fibronectin, vitronectin, laminin, fibrinogen, thrombospondin, and von Willebrand factor, are the target epitope of RGCyteic acid peptide and its derivatives. The tripeptide, RGCysteic acid, has been discovered as a recognizable minimal amino acid sequence by cell binding domains. This sequence can also interfere with immune functions unrelated to integrins.

Thus, it has been discovered that the synthetic RGCysteic acid sequence is to mimic the RGD cell binding domain, and a substitution on the α-carbon of aspartic acid gives a stronger binding affinity to the target integrins. The sulfonic acids in the RGC-peptides are stronger acids than corresponding carboxylic acids in RDG-peptides. This higher polarity of the sulfonic acid group leads to stronger intermolecular bonding. For example, R-G-Cysteic acid, which has a more polarized O—H bond, may form stronger hydrogen bonds than R-G-Aspartic acid, which has a relatively less polarized O—H bond, with the amide groups and/or side chains of the amino acids in the integrin binding site and/or have stronger interactions with metal ions complexed in the integrin binding site.

The most general formulas for the RGCysteic acid sequences of the present invention are as follows:

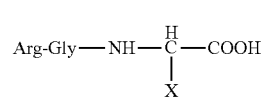

Formula A

Where X=—CH($R_1$)—S(=O)$_2$—Y;
—CH($R_1$)—SH;
CH($R_1$)—OZ;
—CH($R_1$)S(=O)Y;
—CH($R_1$)—O—S(=O)$_2$—$OX_1$; and
CH($R_1$)—O—P(=O)$_2$—$OX_1$; and Wherein Y=OX$_1$, NH$_2$; X$_1$=—H, C$_1$-C$_6$ straight chain alkyl, phenyl;
R$_1$=H, C$_1$-C$_6$ straight chain alkyl, phenyl or SO$_3$H
Z=H, SOH Formula B

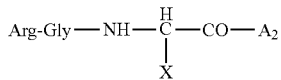

Where X=—CH(R$_1$)—S(=O)$_2$—Y;
—CH(R$_1$)—SH;
CH(R$_1$)—OZ;
—CH(R$_1$)S(=O)Y;
—CH(R$_1$)—O—S(=O)$_2$—OX$_1$; and
—CH(R$_1$)—O—P(=O)$_2$—OX$_1$; and
Wherein Y=OX$_1$, NH$_2$; X$_1$=—H, C$_1$-C$_6$ straight chain alkyl, phenyl;
R$_1$=H, C$_1$-C$_6$ straight chain alkyl, phenyl or SO$_3$H
Z=H, SO$_5$H; and
A$_2$ is selected from: -Phe-Val-Ala, -Phe-Leu-Ala, -Phe-Val-Gly, -Phe-Leu-Gly, -Phe-Pro-Gly, -Phe-Pro-Ala, -Phe-Val, or salt or N-alkylated derivative thereof. Any combination of D-form or L-form of Arg, Gly, Cysteic, Phe, Val, Ala, Leu, Pro, Thr, as well as cyclic form of the above sequence can be used.
Examples of cyclic forms include:

Formula C

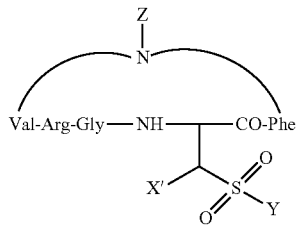

where X' is selected from: H, C$_1$-C$_6$ alkyl, Ph, SO$_3$H; Y=OH, NH$_2$ and Z=H, CH$_3$.

Cyclic forms also include penta and hepta peptides, such as for example a specific compound of General Formula C, namely, Compound 2 (Cyclo-RGCysteic Acid fN(CH$_3$)V), is shown below:

Compound 2

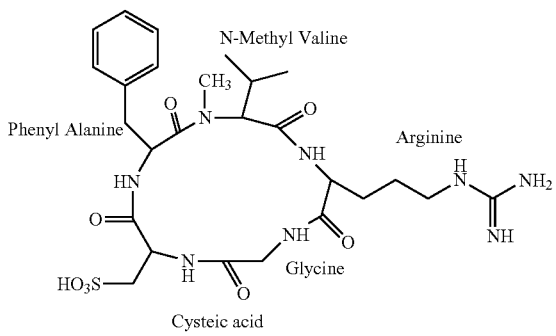

Formula A encompasses General Formulas I-VI described elsewhere herein. Formula B encompasses general formula VII described elsewhere herein.

A$_1$-Arg-Gly-NH—CH(X)—CO-A$_2$    Formula D:

Where X=—CH(R$_1$)—S(=O)$_2$—Y;
—CH(R$_1$)—SH;
CH(R$_1$)—OZ;
CH(R$_1$)S(=O)Y;
—CH(R$_1$)—O—S(=O)$_2$—OX$_1$; and
—CH(R$_1$)—O—P(=O)$_2$—OX$_1$; and
Wherein Y=OX$_1$, NH$_2$; X$_1$=—H, C$_1$-C$_6$ straight chain alkyl, phenyl;
R$_1$=H, C$_1$-C$_6$ straight chain alkyl, phenyl or SO$_3$H
Z=H, SO$_3$H; and
A$_1$ and A$_2$ are selected from: -Phe-Val-Ala, -Phe-Leu-Ala, -Phe-Val-Gly, -Phe-Leu-Gly, -Phe-Pro-Gly, -Phe-Pro-Ala, -Phe-Val, or salt or N-alkylated derivative thereof. Any combination of D-form or L-form of Arg, Gly, Cysteic, Phe, Val, Ala, Leu, Pro, Thr, as well as cyclic form of the above sequence can be used.

The substituted RGCysteic acid sequences includes cyclic RGCysteic acid analogues.

The application of the RGCysteic acid and its derivatives can be made subcutaneously, dermatologically, ophthamically and systemically, by employing a drug delivery system or any pharmaceutically acceptable dosage forms of injection or solid or ointment formulation.

The compounds of the present invention may be administered by any route that is suitable to bring about the intended therapeutic effect including but not limited to: oral, rectal, intravenous, intraarterial, intradermal, subcutaneous, intramuscular, intrathecal, sublingual, buccal, intranasal, transmucosal, transdermal, topical, intraocular, intravitreal, other enteral, other parenteral and/or other possible route(s) of administration.

The compounds of the present invention may be administered at any dosage that provides the intended therapeutic effect while avoiding untoward or toxic effects. Typical dosages at which the compounds of the present invention may be administered to human subjects are in the range of about 1 ng/kg to about 1.0 g/kg.

Where possible and appropriate, compounds of the present invention may optionally be prepared in the form of liposomes or nanoparticles (e.g., nanocapsules). The formation and use of liposomes is generally known to those of skill in the art. Liposomes are formed from phospholipids dispersed in an aqueous medium such that they spontaneously form multilamellar concentric bilayer vesicles sometimes referred to as multilamellar vesicles (MLVs). MLVs are typically from 25 nm to 4 μm in diameter. When sonicated, MLVs form small unilamellar vesicles (SUVs) of about 200 to 500 angstroms in diameters having cores which contain the aqueous solution. In general, when dispersed in an aqueous medium, phospholipids can form various structures other than liposomes, depending on the molar ratio of lipid to water. At low molar lipid to water ratios, liposomes will form. The physical characteristics of liposomes depend on pH, tonicity and the presence or non-presence of divalent cations. Liposomes can interact with cells by different mechanisms, including 1) endocytosis (e.g., phagocytosis of the liposome by cells such as macrophages and neutrophils), adsorption to the cell surface, 2) interaction with cell-surface components, 3) fusion with the plasma cell membrane by insertion of the lipid bilayer of the liposome into the plasma membrane or 4) transfer of liposomal lipids to cellular or subcellular membranes, or vice versa. Varying the liposome formulation can alter which mechanism(s) by which the liposomes will interact with cells in the paranasal sinus, nasal mucosa, etc.

A nanocapsule is any nanoparticle that consists of a shell and a space, in which desired substances may be placed. Techniques for forming nanocapsules are known in the art. Polymeric nanocapsules can be made in specific sizes and shapes. They can be produced as monodisperse particles which have precisely defined physical and chemical properties and, thus, can be tailored to facilitate release of the therapeutic or diagnostic substance in response to particular bimolecular triggering mechanisms, such as pH, mucous flow or other conditions present within the paranasal sinus or other area in the ear, nose or throat where the device is implanted. Nanocapsules can be used in the present invention as "smart drugs" which have specific chemical receptors or binding sites that will bind to specific target cells (e.g., cancer cells or cells associated with inflammatory conditions).

The following are non-limiting examples of formulations for pharmaceutical preparations containing compounds of the present invention. Also included are examples of the safety and/or efficacy demonstrated using exemplary RGC peptides or derivatives in inhibiting cell adhesion. As used herein, the terms "RGCysteic Acid Peptide," "RGC peptide", "RGCys-peptide" and "compounds of the present invention" shall synonymously mean compositions containing the sequence R-G-Cysteic Acid and their derivatives, including but not limited to those defined by General Formulas I-VII and Compounds 1, and 3-5 as described herein.

Example 1

Pharmaceutical Formulations

The following are examples of pharmaceutical formulations I-X, which contain R-G-Cysteic Acid Peptides of the present invention, such as any of those defined by General Formulas I-VII or any of Compounds 1-5 as described herein.

| Formulation I | |
|---|---|
| R-G-Cysteic Acid Peptide (RGCys-peptide) | 0.0001 mg to 10 g |
| NaCl | 0.01 mg to 0.9 g |
| Water | QS to 100.0 mL |
| Formulation II | |
| RGCysteic Acid Peptide (RGCys-peptide) | 0.0001 mg to 10 g |
| EDTA | 0.001 mg to 100 mg |
| NaCl | 0.01 mg to 0.9 g |
| Water | QS to 100.0 mL |
| Formulation III | |
| RGCysteic-peptide | 0.0001 mg to 10 g |
| EDTA | 0.001 mg to 100 mg |
| NaCl | 0.01 mg to 0.9 g |
| Citric Acid | 0.0001 mg to 500 mg |
| Water | QS to 100.0 mL |
| Formulation IV | |
| RGCysteic-peptide | 0.0001 mg to 10 g |
| NaCl | 0.01 mg to 0.9 g |
| Phosphate Buffer to | pH = 3.0-9.0 |
| Water | QS to 100.0 mL |
| Formulation V | |
| RGCysteic-peptide | 0.0001 mg to 10 g |
| EDTA | 0.001 mg to 100 mg |
| NaCl | 0.01 mg to 0.9 g |
| Phosphate Buffer to | pH = 3.0-9.0 |
| Water | QS to 100.0 mL |

| Formulation VI | |
|---|---|
| RGCysteic-peptide | 0.0001 mg to 10 g |
| NaCl | 0.01 mg to 0.9 g |
| Borate Buffer to | pH = 3.0-9.0 |
| Water | QS to 100.0 mL |
| Formulation VII | |
| RGCysteic-peptide | 0.0001 mg to 10 g |
| Hyaluronic Acid Sodium salt | 0.01 to 10% |
| Boric Acid | 0.01 to 1.0% |
| Polyethyleneglycol (PEG 8000) | 0.01 to 10% |
| Sodium Chloride | 0.10 to 0.9% |
| Potassium Chloride | 0.01 to 0.20% |
| Calcium Chloride Dihydrate | 0.001 to 0.05% |
| Magnesium Chloride Hexahydrate | 0.01 to 0.20% |
| Preservative | |
| pH | 4.0-8.0 |
| Water | QS to 100.0 mL |
| Formulation VIII | |
| RGCysteic-peptide | 0.0001 mg to 10 g |
| Hyaluronic Acid Sodium salt | 0.01 to 10% |
| Carboxymethyl Cellulose | 0.01 t0 10% |
| Boric Acid | 0.01 to 1.0% |
| Polyethyleneglycol (PEG 8000) | 0.01 to 10% |
| Sodium Chloride | 0.10 to 0.9% |
| Potassium Chloride | 0.01 to 0.20% |
| Calcium Chloride Dihydrate | 0.001 to 0.05% |
| Magnesium Chloride Hexahydrate | 0.01 to 0.20% |
| Preservative | |
| pH | 4.0-8.0 |
| Water | QS to 100.0 mL |
| Formulation IX | |
| RGCysteic-peptide | 0.0001 mg to 10 g |
| Hyaluronic Acid Sodium salt | 0.01 to 10% |
| Sodium Alginate | 0.01 t0 10% |
| Boric Acid | 0.01 to 1.0% |
| Polyethyleneglycol (PEG 8000) | 0.01 to 10% |
| Sodium Chloride | 0.10 to 0.9% |
| Potassium Chloride | 0.01 to 0.20% |
| Calcium Chloride Dihydrate | 0.001 to 0.05% |
| Magnesium Chloride Hexahydrate | 0.01 to 0.20% |
| Preservative | |
| pH | 3.0-8.0 |
| Water | QS to 100.0 mL |
| Formulation X | |
| RGCysteic-peptide | 0.0001 mg to 10 g |
| Hyaluronic Acid Sodium salt | 0.01 to 10% |
| Alginic Acid | 0.01 t0 10% |
| Boric Acid | 0.01 to 1.0% |
| Polyethyleneglycol (PEG 8000) | 0.01 to 10% |
| Sodium Chloride | 0.10 to 0.9% |
| Potassium Chloride | 0.01 to 0.20% |
| Calcium Chloride Dihydrate | 0.001 to 0.05% |
| Magnesium Chloride Hexahydrate | 0.01 to 0.20% |
| Preservative | |
| pH | 3.0-8.0 |
| Water | QS to 100.0 mL |

Example 2

Comparison of The PVD-Inducing Effects of RGD Peptides and Glycyl-Arginyl-Glycyl-Cysteic-Threonyl-Proline-COOH (GRG Cysteic Acid TP; Compound 1) in Rabbits In this example, the PVD-Inducing Effects of RGD Peptides and Glycyl-Arginyl-Glycyl-Cysteic-Threonyl-Proline-COOH (RGCysteic Acid Peptide; GRG Cysteic Acid TP; Compound 1) were compared in rabbits. The protocol for this study was as follows:

Protocol:
Animal Model
a) 20 Male and Female Rabbits
b) Weighing approximately 1.5-2.5 kg.
c) Divide into 2 groups
i) 10 Rabbits were injected intravitreally with 2.5% RGD solution at pH=6.5
  a) 10 Right Eye injected with 2.5% RGD solution
  b) 5 Left Eye used as BSS Control
  c) 5 Left Eyes injected with 2.5% RGD+0.02% EDTA at pH=6.5
ii) 10 Rabbits were injected intravitreally with 2.5% RGCysteic solution at pH=6.5
  a) 10 Right Eye injected with 2.5% RGCysteic solution at pH=6.5
  b) 10 Left Eye injected with 2.5% RGCysteic solution+ 0.02% EDTA at pH=6.5
Active Chemicals
d) Sodium EDTA—99.0-100.5% from Spectrum Chemical Corp.
e) RGCysteic acid—cGMP supplier (Purity>98%).
f) RGD—cGMP supplier (Purity>98%).
g) BSS solution Both the RGCysteic acid, RGD, RGCysteic acid+Sodium EDTA, RGD+Sodium EDTA, and the BSS solutions were injected into the vitreous cavity 24 hours prior to surgery. The rabbits (10 mg/kg body weight) were anesthetized with an intramuscular injection of 2.0 ml of 1:1 combination of xylazine (100 mg/ml) and Ketamine hydrochloride (100 mg/ml). Pupils are dilated with topical cyclopentolate hydrochloride 1% and Phenylephrine hydrochloride 10%.

All animals were initially examined with slit lamp biomicroscopy and indirect ophthalmoscopy to exclude any animals with pre-existing vitreoretinal abnormalities. The intravitreal injection of 0.10 cc was administered 2 mm posterior to the limbus in the supranasal quadrant using a 30-gauge needle attached to a 1.0 cc syringe. Care must be taken to avoid damage to the lens or retina.

Twenty four hours following injection and immediately before initiation of a mechanical vitrectomy, a B-scan ultrasonography was performed to determine the status of the posterior vitreous and also the liquefaction of the vitreous. A two-port pars plana vitrectomy was performed using an infusion fiberoptic and a vitreous cutter attached to a vitrectomy unit. Following a 30 second core vitrectomy, the vitreous cutter was directed to the peripapillary retinal surface where, using low aspiration (<30 mmHg) a separation of the posterior cortical vitreous from the retinal surface was attempted in 4 quadrants. The sclerotomies were sutured and a postoperative B-Scan ultrasonography was carried out to determine the presence and extent of any PVD present in each quadrant. The animals were euthanized with intracardiac sodium pentobarbital injections, and the eyes were immediately enucleated.

Classification of Liquefaction of the Vitreous and PVD was graded following this grading system to evaluate the extent of PVD based on the postoperative B-Scan ultrasound examination;
  Grade 0. a) No detachment of the posterior Vitreous is observed.
    b) Vitreous Liquefaction
  Grade 1. a) Consists of eyes in which the vitreous is detached in 2 or less quadrants.
    b) Vitreous Liquefaction
  Grade 2. a) Consists of eyes in which the vitreous is detached in 3 or more quadrants, but with remaining focal attachments along the medullary rays
    b) Vitreous Liquefaction
  Grade 3. a) Consists of eyes in which the vitreous is totally detached from the retinal surface
    b) Vitreous Liquefaction All eyes underwent a sharp razor penetration at the superior pole sub-adjacent to the pars plana immediately after enucleating to insure rapid penetration of fixative. Care was taken to avoid damage to the adjacent retina and lens. The eyes were immersed in 2% paraformaldehyde plus 2.5% glutaraldehyde for a minimum of 24 hours at 4 degrees Celsius. A unique posterior calotte was removed, dehydrated in methanol, and dried in carbon dioxide to the critical point, sputter-coated in gold and photographed using the scanning electron microscope.

Results:

| Injection: 2.5% RGCysteic acid Group 1. At Baseline all Animals have no PVD in both eyes | | | | | |
|---|---|---|---|---|---|
| Eye Examined | Animal 1 | Animal 2 | Animal 3 | Animal 4 | Animal 5 |
| O D Treated | Grade 3 - 4 Q Vitreous totally Detached | Grade 3 - 4 Q Vitreous totally Detached | Grade 2 - 3 Q Vitreous detached in 3 or more Q | Grade 3 - 4 Q Vitreous totally Detached | Grade 1 - 2 Q Vitreous detached in 2 or less Q |
| O S Control | Grade 0 | Grade 0 | Grade 0 | Grade 0 | Grade 0 |

| Injection: 2.5% of RGD Group 2. At Baseline all Animals have no PVD in both eyes | | | | | |
|---|---|---|---|---|---|
| Eye Examined | Animal 1 | Animal 2 | Animal 3 | Animal 4 | Animal 5 |
| O D Treated | Grade 3 - 4 Q Vitreous totally Detached | Grade 2 - 3 Q Vitreous detached in 3 or more Q | Grade 1 - 2 Q Vitreous detached in 2 or less Q | Grade 3 - 4 Q Vitreous totally Detached | Grade 3 - 4 Q Vitreous totally Detached |
| O S Control | Grade 0 | Grade 1 - 2 Q Vitreous detached in 2 or less Q | Grade 3 - 4 Q Vitreous totally Detached | Grade 1 - 2 Q Vitreous detached in 2 or less Q | Grade 0 |

Injection: 2.5% RGCysteic acid + 0.02% NaEDTA
Group 3. At Baseline all animals have no PVD in both eyes

| Eye Examined | Animal 1 | Animal 2 | Animal 3 | Animal 4 | Animal 5 |
|---|---|---|---|---|---|
| O D Treated | Grade 1 - 2 Q Vitreous detached in 2 or less Q | Grade 3 - 4 Q Vitreous totally Detached | — | Grade 3 - 4 Q Vitreous totally Detached | Grade 1 - 2 Q Vitreous detached in 2 or less Q |
| O S Control | Grade 1 - 2 Q Vitreous detached in 2 or less Q | Grade 0 | — | Grade 2 - 3 Q Vitreous detached in 3 or more Q | Grade 0 |

Injection: 2.5% RGD + 0.02% NaEDTA
Group 4. At Baseline all animals have no PVD in both eyes

| Eye Examined | Animal 1 | Animal 2 | Animal 3 | Animal 4 | Animal 5 |
|---|---|---|---|---|---|
| O D Treated | Grade 3 - 4 Q Vitreous totally Detached | Grade 0 | Grade 3 - 4 Q Vitreous totally Detached | Grade 0 | Grade 1 - 2 Q Vitreous detached in 2 or less Q |
| O S Control | Grade 2 - 3 Q Vitreous detached in 3 or more Q | Grade 2 - 3 Q Vitreous detached in 3 or more Q | Grade 0 | Grade 0 | Grade 0 |

The results of the kinetic study in Example 4 of this study show that RGD and RGCysteic acid (GRG Cysteic Acid TP; Compound 1) have similar properties and injection of 2.5% RGCysteic acid intravitreally causes complete separation of the vitreous from the retina in 24 hours, and in addition the vitreous of both the RGD and the RGCysteic acid rabbits are completely liquefied.

Over all, the activity of RGCysteic acid is equal or slightly better than that of RGD in inducing complete PVD in the rabbits and liquefying the vitreous. This is possibly due to its stronger competitive binding ability to the binding sites of integrin-extracellular matrix interactions than RGD. As described elsewhere herein, sulfonic acids are stronger acids than corresponding carboxylic acids. This higher polarity of the sulfonic acid group leads to stronger intermolecular bonding. For example, R-G-Cysteic acid, which has a more polarized O—H bond, may form stronger hydrogen bonds than R-G-Aspartic acid, which has a relatively less polarized O—H bond, with the amide groups and/or side chains of the amino acids in the integrin binding site and/or have stronger interactions with metal ions complexed in the integrin binding site.

The results also indicate that when these compounds are administered with 0.02% Sodium Edetate, the activity of both RGD as well as RGCysteic acid are not altered.

The results also show that there were no adverse effects or adverse safety effects from the intravitreal injection of the RGCysteic acid compound Compound 1 or the RGD compound.

Example 3

Safety Study of Multiple Injections of RGC Peptide Compound 1 (GRG Cysteic Acid TP) in Rabbit Eyes In this example, multiple injections of RGC Peptide Compound 1 were administered to the eyes of 5 Male and 4 Female New Zealand Rabbits weighing approximately 1.5-2.5 kg. and the eyes were examined as described in the following paragraphs.

The study then protocol was as follows:
A) Baseline Examinations: At baseline the right and the left eyes of all 9 rabbits were examined slit lamp biomicroscopy and indirect ophthalmoscopy to confirm that no animals had pre-existing vitreoretinal abnormalities. In addition β-scan ultrasonography as well as ERG scans were performed on the left and right eyes of all 9 animals to obtain baseline readings.
B) Experimental Treatments: All 9 Rabbits then received intravitreal injections of either RGC solution or saline (control). The treatment solutions were prepared as follows:
RGC Solution: a 2.5 mg/100 µl solution of RGC Compound 1 containing 0.02 mg of disodium EDTA+0.80 mg of sodium chloride and USP sterile Water for injection having a pH adjusted to 6.5.
Saline (control): a USP Isotonic sterile saline solution having an adjusted pH of 6.5.
The dosing proceeded as follows:
1) The right eye of each of the 9 rabbits was injected intravitreally with 100 of the 2.5 mg/100 µl RGC Solution (delivering a dose=2.5 mg of Compound 1)
2) The Left eye of each of the 9 rabbits was injected intravitreally with 100 µl of the Saline (control).
3) One day after the initial intravitreal injections, the right and the left eyes of all 9 Rabbits were examined, by slit lamp biomicroscopy and indirect ophthalmoscopy to check if any of the rabbits have any adverse effects from the injection.
4) On the $7^{th}$ day after the $1^{st}$ injections, the right and the left eyes of all 9 Rabbits were again examined by slit lamp biomicroscopy and indirect ophthalmoscopy to determine if any of the rabbits exhibited adverse effects from the injection. In addition ERG scan were performed on all right and left eyes of all the animals to determine if there were any changes from baseline
5) A group of 3 rabbits, numbers 901, 904 and 909, was then randomly selected and mechanical vitrectomy was performed on the right and left eyes of those 3 selected animals to determine the status of the posterior vitreous.
6) The 3 randomly selected animals, numbers 901, 904 and 909, were euthanized with intracardiac sodium pentobarbital injections, and the eyes were immediately enucleated. All eyes underwent a sharp razor penetration at the superior pole sub-adjacent to the pars plana immediately after enucleation to insure rapid penetration of fixative. Care was taken to avoid damage to the adjacent retina and lens. The eyes were immersed in 2% paraformaldehyde plus 2.5% gluteraldehyde for a minimum of 24 hours at 4 degrees Celsius. A unique posterior calotte was removed, dehydrated in methanol, and dried in carbon dioxide to the critical point, sputter-coated in gold and photographed using the scanning electron microscope. The other samples were subjected to Histopathological examination.

The remaining 6 Rabbits, numbers 902, 903, 905, 906, 907 and 908 were injected a second time 7 days post first injection.

1) The right eye of each of the 6 remaining rabbits was again injected intravitreally with 100 of the 2.5 mg/100 µl RGC Solution (delivering a second 2.5 mg dose of Compound 1)

2) The left eye of each of the 6 remaining rabbits was again injected intravitreally with 100 µl of the Saline (control).

3) One day after the $2^{nd}$ intravitreal injections, the right and the left eyes of all 6 remaining rabbits were examined by slit lamp biomicroscopy and indirect ophthalmoscopy to check if any of the rabbits have any adverse effects from the injection.

4) On the $7^{th}$ day after the $2^{nd}$ injections, the right and the left eyes of all 6 reaming rabbits were examined, by slit lamp biomicroscopy and indirect ophthalmoscopy to check for any adverse effects from the injections. In addition ERG scans of the left and right eyes of all the animals were run to determine if there were any changes from the baseline.

5) Three rabbits, numbers 902, 903, and 907, were then randomly selected from the remaining 6 animals and mechanical vitrectomy was performed on the right and left eyes of those 3 randomly selected animals to determine the status of the posterior vitreous.

6) The 3 randomly selected animals, numbers 902, 903, and 907 were then euthanized with intracardiac sodium pentobarbital injections, and the eyes were immediately enucleated. All eyes underwent a sharp razor penetration at the superior pole sub-adjacent to the pars plana immediately after enucleation to insure rapid penetration of fixative. Care was taken to avoid damage to the adjacent retina and lens. The eyes were immersed in 2% paraformaldehyde plus 2.5% gluteraldehyde for a minimum of 24 hours at 4 degrees Celsius. A unique posterior calotte was removed, dehydrated in methanol, and dried in carbon dioxide to the critical point, sputter-coated in gold and photographed using the scanning electron microscope. The other samples were subjected to Histopathological examination.

The remaining group of 3 Rabbits, numbers 905, 906, and 908, were then injected a third time, 14 days after the first injection, as follows:

1) The right eye of each of the 3 remaining rabbits was again injected intravitreally with 100 of the 2.5 mg/100 µl RGC Solution (delivering a third 2.5 mg dose of Compound 1)

2) The left eye of each of the 3 remaining rabbits was again injected intravitreally with 100 µl of the Saline (control).

3) One day after the $3^{rd}$ intravitreal injections, the right and the left eyes of all 6 remaining rabbits were examined, by slit lamp, biomicroscopy and indirect ophthalmoscopy to check if any of the rabbits have any adverse effects from the injection.

4) On the $7^{th}$ day after the $3^{rd}$ injections, the right and the left eyes of all 3 remaining rabbits were again examined by slit lamp biomicroscopy and indirect ophthalmoscopy to check for any adverse effects from the injections. In addition ERG scans of the left and right eyes of all the animals were run to determine if there were any changes from the baseline.

5) Mechanical vitrectomy was performed on the right and left eyes of the 3 remaining animals (Nos. 905, 906 and 908) to determine the status of the posterior vitreous.

6) The 3 remaining animals (Nos. 905, 906, and 908) were euthanized with intracardiac sodium pentobarbital injections, and the eyes were immediately enucleated. All eyes underwent a sharp razor penetration at the superior pole sub-adjacent to the pars plana immediately after enucleation to insure rapid penetration of fixative. Care was taken to avoid damage to the adjacent retina and lens. The eyes were immersed in 2% paraformaldehyde plus 2.5% gluteraldehyde for a minimum of 24 hours at 4 degrees Celsius. A unique posterior calotte was removed, dehydrated in methanol, and dried in carbon dioxide to the critical point, sputter-coated in gold and photographed using the scanning electron microscope. The other samples were subjected to Histopathological examination.

3) Active Chemicals

The active chemicals used in this study were as follows:
a. Disodium EDTA—99.0-100.5% from Spectrum Chemical Corp.
b. RGC Peptide (Compound 1)
c. USP sterile isotonic saline solution 4) Study Formulations a) RGC Solution: 2.5 mg/100 µl solution of RGC containing 0.02 mg of disodium EDTA+0.80 mg of sodium chloride and USP sterile water for injection adjusted to a pH=6.5. Sterile filter through a 0.22µ filter into a 2.0 mL vial.

b) Saline (Control): USP Isotonic sterile saline solution pH adjusted 6.5. Sterile filtered through a 0.22µ filter into a sterile vial.

5) Anesthesia for Injection Preparation a. Intramuscular injection of 2.0 mL of a 1:1 combination of xylazine (100 mg/ml) and Ketamine hydrochloride (100 mg/ml)

b. Pupils were dilated with topical cyclopentolate hydrochloride 1% and Phenylephrine hydrochloride 10%

6) Intravitreal Injection Preparation:

A sterile vial containing the RGC solution containing 2.5 mg/100 µl and isotonic sterile saline solution, pH adjusted to 6.5 was provided.

Prior to the injection, the investigator confirmed that there was 0.10 cc (100 micro liters) of solution in the 1.0 cc syringe.

7) Injection Procedure:

Since the intravitreal injections do not result in a level of visual disability sufficient to disrupt the normal daily activity of the rabbits, this is not considered a major survival procedure according to the animal resolution of the Association for Research in Vision and Ophthalmology guidelines.

Both the RGC solution as well as the sterile saline solutions was injected into the vitreous cavity after the baseline examination of slit lamp Biomicroscopy, Ophthalmoscopy and ERG was completed on the Rabbits.

The Rabbits (10 mg/kg body weight) were anesthetized with an intramuscular injection of 2.0 ml of 1:1 combination of xylazine (100 mg/ml) and Ketamine hydrochloride (100 mg/ml). Pupils were dilated with topical cyclopentolate hydrochloride 1% and Phenylephrine hydrochloride 10%.

All animals were initially examined with slit lamp biomicroscopy and indirect opthalmoscopy to exclude any animals with pre-existing vitreoretinal abnormalities. The intravitreal injection of 0.10 cc was administered 2 mm posterior to the limbus in the supronasal quadrent using a 30-gauge needle attached to a 1.0 cc syringe. Care was taken to avoid damage to the lens or retina.

Seven (7) days following injection a mechanical Vitrectomy was performed on the animals. A two-port pars plana vitrectomy was performed using an infusion fiberoptic and a vitreous cutter attached to a vitrectomy unit. Following a 30 second core vitrectomy, the vitreous cutter was directed to the peripapillary retinal surface where, using low aspiration (<30 mmHg) a separation of the posterior cortical vitreous from the retinal surface was attempted in 4 quadrants. The animals were euthanized with intracardiac sodium pentobarbital injections, and the eyes were immediately enucleated.

All eyes underwent a sharp razor penetration at the superior pole sub-adjacent to the pars plana immediately after enucleation to insure rapid penetration of fixative. Care was taken to avoid damage to the adjacent retina and lens. The eyes were immersed in 2% paraformaldehyde plus 2.5% gluteraldehyde for a minimum of 24 hours at 4 degrees Celsius. A unique posterior calotte was removed, dehydrated in methanol, and dried in carbon dioxide to the critical point, sputter-coated in gold and photographed using the scanning electron microscope.

Analysis of Results

The data on the Safety between eyes treated with RGC solution and sterile saline solution was analyzed for safety using the following techniques:
 i) Slit lamp biomicroscopy;
 ii) Ophthalmoscopy;
 iii) ERG;
 iv) Histopathology; and
 v) Electron microscopy.

Safety Profile:

First Intravitreal administration of 100l of 2.5% RGC solution to the group of nine Rabbits numbers 901, 902, 903, 904, 905, 906, 907, 908, 909, was not associated with any significant toxicity at all time points. There was no significant difference in reported adverse effects between the 2.5% RGC group and the isotonic saline solution group. This lack of toxicity was determined by clinical examination, indirect ophthalmoscopy and ultrasound 1-scan and mechanical vitrectomy.

Slit lamp biomicroscopy was performed at all study visits and focused on the lids, conjunctiva and sclera, cornea, endothelial changes, anterior chamber reaction, iris, lens and capsule, as well as the anterior vitreous for signs for inflammation demonstrate a near complete lack of inflammatory reaction to intravitreal injections of 100 µl of 2.5% RGC solution and the isotonic saline solution group. At all study points and in all study groups there did not appear to be any signs of significant toxicity induced by the test articles.

Clinical evaluation of the posterior segment was also followed throughout the study to ensure that there was no significant retinal toxicity present. Indirect ophthalmoscopy as well as slit lamp fundus evaluations were carried out at each evaluation time point with specific attention to any signs of retinal toxicity. The posterior segment was evaluated for any changes in vitreous density, vitreous liquefaction, vitreous attachment, and possible hemorrhage. The retina was evaluated for any signs of RPE toxicity, retinal vascular compromise retinal hemorrhage, exudates, retinal tears, breaks, or detachments. There were no RPE changes at baseline prior to treatment, at all study points and in all study groups there did not appear to be any signs of significant posterior segment changes induced by the test articles. It is important to note that ERG scans performed on the nine animals prior to the intravitreal injections, as well as ERG scans performed on all the animals 1 day and 7 days post injection did not appear to cause any signs of significant change or toxicity induced by the test articles.

The second Intravitreal administration of 100 µl of 2.5% RGC solution to the group of six Rabbits numbers 902, 903, 905, 906, 907, 908, was not associated with any significant toxicity at all time points. There was no significant difference in reported adverse effects between the 2.5% RGC group and the isotonic saline solution group. This lack of toxicity was determined by clinical examination, indirect ophthalmoscopy and ultrasound β-scan and mechanical vitrectomy.

Slit lamp biomicroscopy was performed at all study visits and focused on the lids, conjunctiva and sclera, cornea, endothelial changes, anterior chamber reaction, iris, lens and capsule, as well as the anterior vitreous for signs for inflammation demonstrate a near complete lack of inflammatory reaction to intravitreal injections of 100 µl of 2.5% RGC solution and the isotonic saline solution group. At all study points and in all study groups there did not appear to be any signs of significant toxicity induced by the test articles.

Clinical evaluation of the posterior segment was also followed throughout the study to ensure that there was no significant retinal toxicity present. Indirect ophthalmoscopy as well as slit lamp fundus evaluations were carried out at each evaluation time point with specific attention to any signs of retinal toxicity. The posterior segment was evaluated for any changes in vitreous density, vitreous liquefaction, vitreous attachment, and possible hemorrhage. The retina was evaluated for any signs of RPE toxicity, retinal vascular compromise retinal hemorrhage, exudates, retinal tears, breaks, or detachments. There were no RPE changes at baseline 7 days prior to the second treatment, at all study points and in all study groups there did not appear to be any signs of significant posterior segment changes induced by the test articles. It is important to note that ERG scans performed on the six animals for a second time post the intravitreal injections, as well as ERG scans performed on all the animals 8 days and 14 days post injection did not appear to cause any signs of significant change or toxicity induced by the test articles.

The third Intravitreal administration of 100 µl of 2.5% RGC solution to the group of six Rabbits numbers 905, 906, 908, was not associated with any significant toxicity at all time points. There was no significant difference in reported adverse effects between the 2.5% RGC group and the isotonic saline solution group. This lack of toxicity was determined by clinical examination, indirect ophthalmoscopy and ultrasound 1-scan and mechanical vitrectomy.

Slit lamp biomicroscopy was performed at all study visits and focused on the lids, conjunctiva and sclera, cornea, endothelial changes, anterior chamber reaction, iris, lens and capsule, as well as the anterior vitreous for signs for inflammation demonstrate a near complete lack of inflammatory reaction to intravitreal injections of 100 µl of 2.5% RGC solution and the isotonic saline solution group. At all study points and in all study groups there did not appear to be any signs of significant toxicity induced by the test articles.

Clinical evaluation of the posterior segment was also followed throughout the study to ensure that there was no significant retinal toxicity present. Indirect ophthalmoscopy as well as slit lamp fundus evaluations were carried out at each evaluation time point with specific attention to any signs of retinal toxicity. The posterior segment was evaluated for any changes in vitreous density, vitreous liquefaction, vitreous attachment, and possible hemorrhage. The retina was evaluated for any signs of RPE toxicity, retinal vascular compromise retinal hemorrhage, exudates, retinal tears, breaks, or detachments. There were no RPE changes at baseline 14 days prior to the third treatment, at all study points and in all study groups there did not appear to be any signs of significant posterior segment changes induced by the test articles. It is important to note that ERG scans performed on the three animals for a third time post the intravitreal injections, as well as ERG scans performed on all the animal 15 days and 21 days post injection did not appear to cause any signs of significant change or toxicity induced by the test articles.

Example 4

Anti-Adhesive Properties of RGC Peptides: Kinetic Study of Wound Healing with Compound 1 (GRG Cysteic Acid TP), Cyclic-RGD and RGE In this example, in a model of wound healing, it has been demonstrated that RGC peptides have anti-adhesive properties and therefore can prevent development of many pathological vitreoretinal diseases and can inhibit metastases in human melanoma and colon cancer cells.

To test the anti-adhesive properties of RGC peptides in vitro, a wound-healing assay was performed with human umbilical vein endothelial cells (HUVEC). HUVEC were seeded and allowed to grow to a confluent monolayer on a fibronectin coated surface. A wound (a scratch rift) was created by dragging a small pipette tip across the HUVEC monolayer. The cells were then incubated in fresh growth medium containing the RGC peptide (Compound 1; 10 mM), and the wound area was imaged in five different fields at various time points (0, 4, 8, 12, 16, 20, 24 hours) to determine the kinetics of wound closure. The level of wound closure was quantified by determining the fraction of the original wound area that was re-occupied by HUVEC through cellular adhesion, migration and proliferation.

In control studies, the following peptides were used in place of RGC (Compound 1): cyclic-RGD peptide (1 mM), positive control) and RGE peptide (1 mM, negative control).

The effect of the peptides on the kinetics of wound healing is presented in FIG. 1.

The results are shown as a percentage of the original area. The error bars correspond to the standard deviation in wound size across 2-6 independent trials.

The results of the kinetics of HUVEC wound closure show that the RGC peptide inhibits HUVEC wound healing by 70% after 24 hours, while Cyclic RGD (RGD-based peptide; N-methylated cyclic-RGDf-N(Me)V; Cilengitide) inhibits HUVEC wound healing by 45% after 24 hours. These were both compared to a negative control RGE peptide that inhibited HUVEC wound healing by 0% after 24 hours. The effect of RGC (Compound 1) is quantitatively comparable to the activity of the RGD-based peptide, a well established inhibitor of integrin binding activity. Further, RGC peptide exhibits similar properties to the activities of the RGD-based peptide without apoptosis of the HUVEC cells.

As described elsewhere herein, the strong adhesion between the vitreous and the retina could account for eventual development of many pathological vitreoretinal diseases such as vitreomacular traction, proliferative diabetic retinopathy, macular hole, age related macular degeneration and floaters. Thus, an atraumatic non-invasive approach to achieve a Posterior Vitreous Detachment, other than the mechanical separation of the vitreous from the inner retinal surface, is highly desirable (see Tezel, T. H. et al, Retina (1998) 18: 7-15; and Verstraeten, T. C, et al., Arch. Ophthalmol. (1993) 111: 849-854).

As described elsewhere herein, it is believed that the ECM components, particularly collagen fibrils of the cortical vitreous, are anchored to the inner surface of the retina through integrin binding sites (see Foos, R. Y., Invest. Ophthalmol. Vis. Sci. (1972) 11:801-808) in the inner limiting lamella (ILL). It is also known that major adhesive glycoproteins of the ILL in the eye such as fibronectin and laminin, are heavily linked to integrins (see Curtis, T. M. et al., Am. J. Physiol., (1995) 269: L248-L260; Elner, S. G., et al., IOVS (1996) 37:696-701; and Horman, S. M, et al., Am. J. Physiol. (1995) 269: L248-L260) through the RGD (Arg-Gly-Asp) sequences and several integrins bind through RGD motif present in ECM proteins. Further, it is known that fibronectin binds to several other integrins besides $\alpha_v\beta_3$, whereas vitronectin is $\alpha_v\beta_3$-specific.

The primary connection of the integrins to the ECM involves the Arg-Gly-Asp(RGD) sequence and the RGD sequence binds to a shallow crevice located between the α- and β-subunits of the integrin head (see Xiong, et al., Science (2002) 296: 151-155). Such binding helps modulate various cellular signaling pathways, including cell adhesion, migration, differentiation, angiogenesis and wound healing (see Ruoslahti, E., et al., Science (1987) 238: 491-497; and J. Clin. Invest. (1991) 87: 1-5).

Since the vitreous extracellular matrix; e.g., collagen fibrils are connected to the cellular retina by the integrin binding sites, intravitreal injection of RGC peptides (oligopeptides) could release the RGD motif of the vitreous extracellular matrix from the cellular retina by a competitive binding to the same integrin receptor sites.

Several investigators (see Ruoslahti, E. et al., Science (1987) 238: 491-497; Hynes, R. A., et al., Cell (1992) 68: 303-322; and Humphries, M. J., J. Cell Sci., (1990) 97: 585-592) demonstrated that many integrins ($\alpha_v\beta_3$, $\alpha_5\beta_1$, $\alpha_{11}\beta_3$, etc.) can be inhibited by small peptides that possess the RGD sequence motif. It is also well documented that that $\alpha_v\beta_3$ and $\alpha_5\beta_1$ integrins, as well as vitronectin and fibronectin, were upregulated in tumors such as human melanoma cells (see Nip, J., J. Clin. Invest., (1992) 90: 1406-1413), human breast cancer cells (see Rong, L. et al., Invest. Ophthalmol. Vis. Sci. (2009) 50: 5988-5996), and human retinal pigment epithelial cells (Peter C. Brooks, et al., J. Clin. Invest., (1995) 96: 1815-1822). Thus it has been demonstrated that there is good correlation between metastatic potentials of human melanoma cells and adhesion of melanoma cells to lymph node vitronectin via the $\alpha_v\beta_3$ integrin receptor and that the adhesion was inhibited by an RGD containing peptide (Nip, J., J. Clin. Invest., (1992) 90: 1406-1413). This demonstrates that RGDpeptides can be an important anti-angiogenic agents.

Further, it has been demonstrated in a human colon cancer cell line that when there is significant increase in cell adhesion, then there is increased metastatic activity (Lehmann, M., Cancer Res., (1994), 54: 2102-2107). Therefore agents that inhibit cell adhesion effectively inhibit colon cancer and melanoma from metastasizing.

Based on the results of the wound healing study where RGC has been shown to inhibit cell adhesion, and upon extrapolation of the metastatic potential of RGD in the Melanoma and Colon cancer models, RGC peptides and their derivatives can effectively inhibit tumor metastases, for example, in melanoma and colon cancer.

Example 5

Use of RGC Peptides for Directing or Delivering Agents to Tumors

In this example, a dimeric RGC Peptide-Paditaxel conjugate (Compound 3), shown below, is provided. This composition is useful as an antitumor agent. The dimeric RGC Peptide selectively binds to integrin receptors that are highly expressed in certain cancer cells and is useful to treat certain metastatic cancers such as, for example, metastatic breast cancer, by inhibiting cell adhesion.

Compound 3

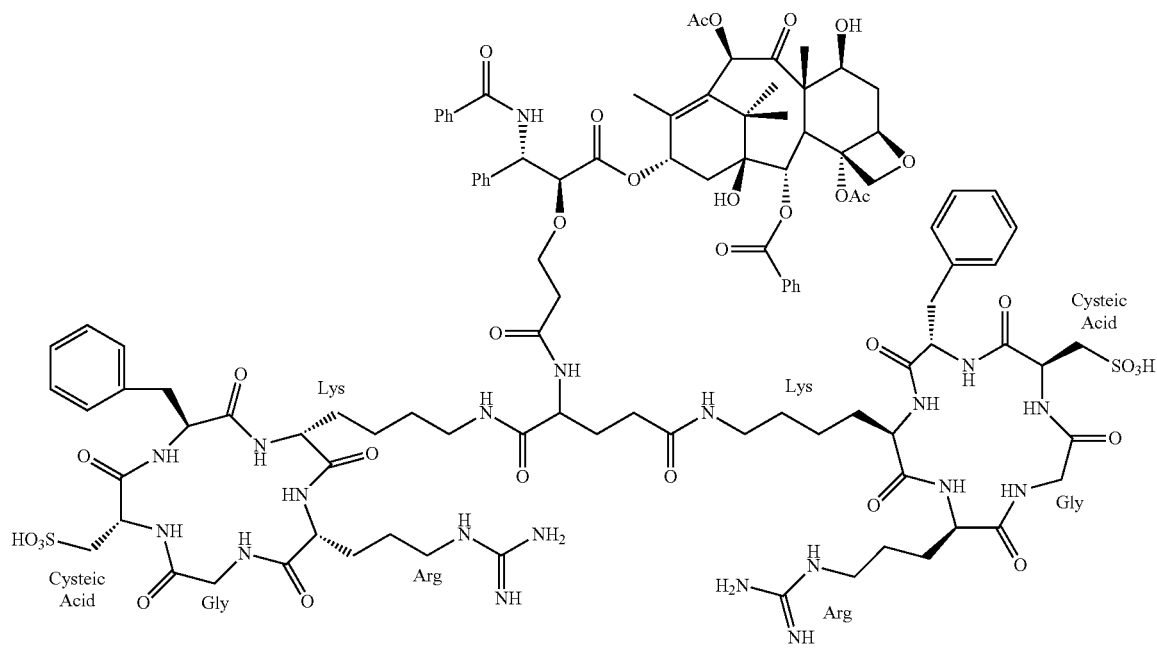

The synthesis and mechanisms of action, biodistribution and tumor selectivity of the corresponding RGD analogue of Compound 3 are as described in Chen, X., et al.; Synthesis and Biological Evaluation of Dimeric RGD Peptide-Paclitaxel Conjugate as a Model for Integrin-Targeted Drug Delivery; J. Med. Chem., (2005) 48 (4): 1098-1106).

Although Compound 3 comprises a particular anti-tumor agent, Paclitaxel, bound to dimeric RGC peptide, it is to be appreciated that this aspect of the invention includes all monomeric or multimeric forms of RGC peptides bound to any feasible diagnostic or therapeutic agents that may be useful in diagnosing, imaging or treating a tumor or other integrin-containing tissue or structure. Examples of antitumor substances that may be bound to monomeric or multimeric RGC peptides in accordance with this invention may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), anti-angiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, *bacillus* calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogs/congeners and derivatives of such compounds as well as other antitumor agents not listed here.

Example 6

$^{64}$CU-Labeled Multimeric RGC Peptides for Imaging of Integrin-Expressive Tumors In this example, $^{64}$CU-Labeled tetrameric and octameric RGC peptides of the present invention (Compounds 4 and 5 respectively), shown below, are useful as radiotherapeutic agents for imaging and diagnostic purposes (e.g., radiolabeling of tumors for PET scanning) as well as for directing or delivering therapeutic agents to tumors or other cells which express integrins, such as tumors which express $\alpha_v\beta_3$ integrins.

Compound 4

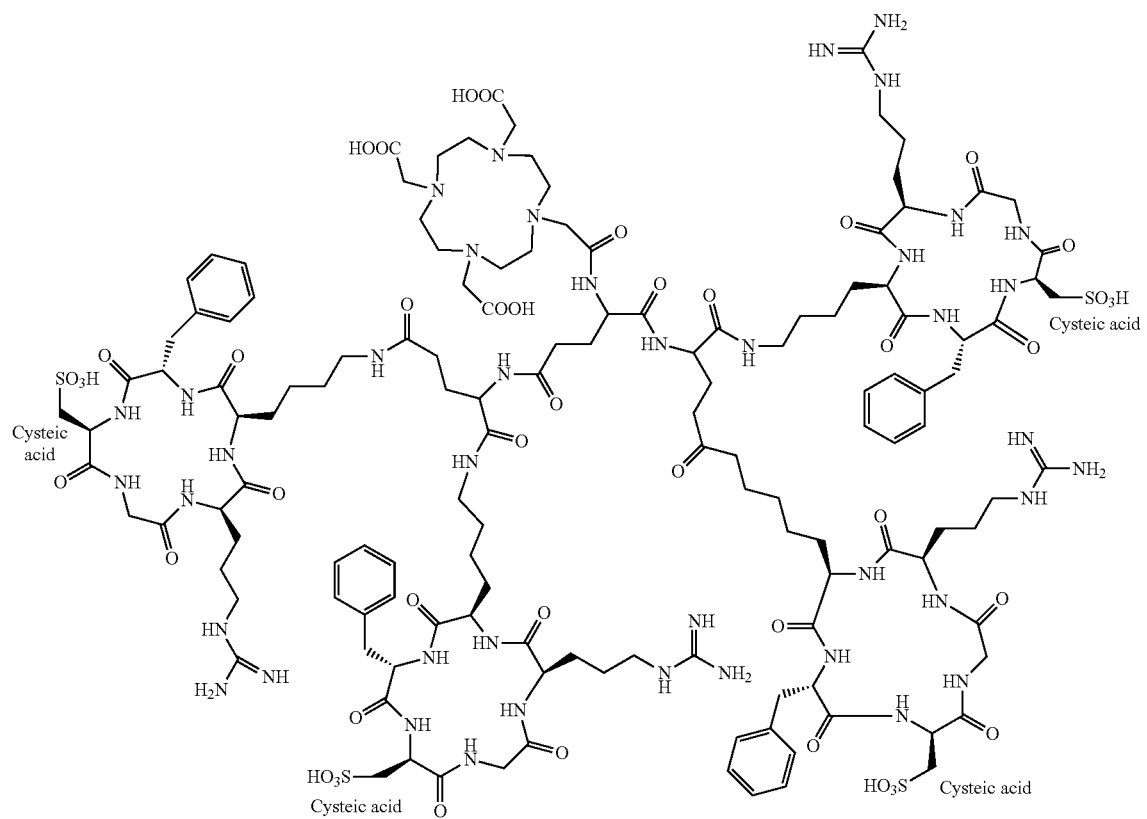

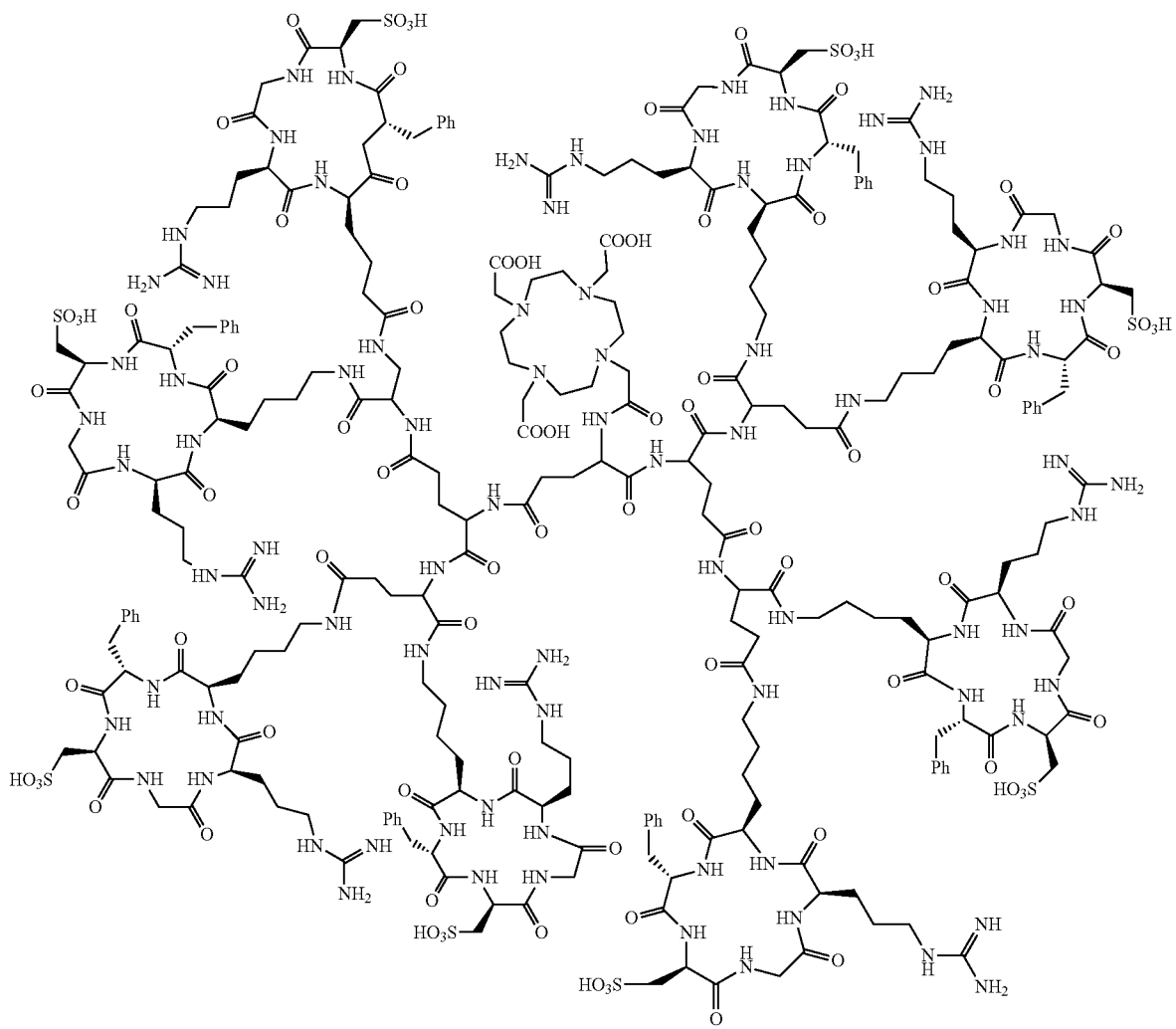

Compound 5

The synthesis and mechanisms of action, biodistribution, tumor selectivity and PET related use of the corresponding RGD analogues of Compounds 4 and 5 are as described in Li, Z. et al., $^{64}$CU-Labeled Tetrameric and Octameric RGD Peptides for Small-Animal PET of Tumor $\alpha_v\beta_3$ Integrin Expression; J. Nucl. Med. 48 (7) pp. 1162-1171 (2007).

As used herein, any reference to treating or treatment of a disease or disorder shall be construed to include preventing or prevention of the disease or disorder before it has occurred or been detected as well as treating the disease or disorder after it has occurred or has been detected.

It is to be appreciated that the invention has been described here above with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims. All publications and patent documents cited herein are hereby incorporated by reference in their entirety for all purposes to the same extent as if each were so individually denoted.

What is claimed is:

1. A method for treating a disorder selected from: retinopathy, diabetic retinopathy, macular hole, vitreomacular traction, age related macular degeneration, wet macular degeneration, retinal neovascularization; retinal neovascularization due to diabetic retinopathy and retinal neovascularization due to retinal vein occlusion, in an eye of a subject who suffers from said disorder, said method comprising administering to the subject an effective amount of a compound which comprises Glycinyl-Arginyl-Glycinyl-Cysteic acid-Threonyl-Proline-COOH (SEQ ID NO: 2) or which has the formula:

X1-R-G-Cysteic Acid-X where X and X1 are selected from: Phe-Val-Ala, -Phe-Leu-Ala, -Phe-Val-Gly, -Phe-Leu-Gly, -Phe-Pro-Gly, -Phe-Pro-Ala, -Phe-Val; or from Arg, Gly, Cysteic acid, Phe, Val, Ala, Leu, Pro, Thr and salts, and any combinations of any D-isomers and L-isomers thereof.

2. A method according to claim 1 wherein the compound comprises SEQ ID NO: 2 and has the structural formula:

Compound 1

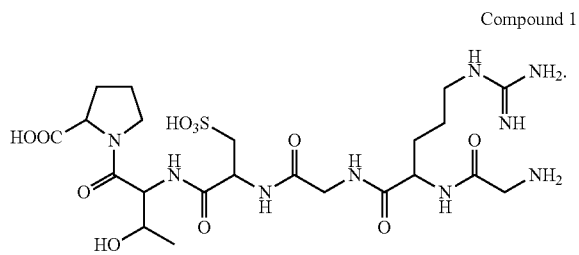 [SMILES: CC(O)C(NC(=O)C(CS(=O)(=O)O)NC(=O)CNC(=O)C(CCCNC(=N)N)NC(=O)CN)C(=O)N1CCCC1C(=O)O]

3. A method according to claim 1 wherein the compound comprises Glycinyl-Arginyl-Glycinyl-Cysteic acid-Threonyl-Proline-COOH (SEQ ID NO: 2).

4. A method according to claim 1 wherein the disorder causes vitreomacular traction and wherein the administration of the compound deters said vitreomacular traction.

5. A method according to claim 1 wherein the compound is injected into an eye of the subject.

6. A method according to claim 5 wherein the compound is injected intravitreally.

7. A method according to claim 1 wherein the compound is administered topically to an eye of the subject.

8. A method according to claim 7 wherein the compound is contained in a liquid or gel preparation for topical administration to said eye.

9. A method according to claim 1 wherein the compound is administered by intravitreal injection to induce posterior vitreal detachment and/or vitreolysis in the eye prior to performance of a vitrectomy and wherein the method further comprises the step of performing said vitrectomy after the compound has induced said posterior vitreal detachment and/or vitreolysis in the eye.

10. A method according to claim 1 wherein the disorder causes inflammation and wherein the administration of the compound reduces said inflammation.

11. A method according to claim 1 wherein the disorder causes abnormal cell adhesion and wherein the administration of the compound deters said abnormal cell adhesion.

12. A method according to claim 11 wherein the administration of the compound deters adhesion to a cell adhesion motif selected from: fibronectin, vitronectin, laminin, fibrinogen, thrombospondin, and von Willebrand factor.

13. A method according to claim 1 wherein the disorder causes abnormal cellular apoptosis and wherein the administration of the compound reduces said abnormal cellular apoptosis.

14. A method according to claim 1 wherein the disorder causes a pathological integrin-extracellular matrix interaction and wherein the administration of the compound deters said pathological integrin-extracellular matrix interaction.

15. A method according to claim 1 wherein the disorder causes a pathological interaction between fibroblasts and glycoprotein components of extracellular matrix and wherein the administration of the compound deters said pathological interaction between fibroblasts and glycoprotein components of extracellular matrix.

16. A method according to claim 1 wherein the disorder causes abnormal angiogenesis and wherein the administration of the compound reduces said abnormal angiogenesis.

* * * * *

SEQUENCE LISTING

<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: Cyclic peptide
<220> FEATURE:
<221> NAME/KEY: MOD_RES
<222> LOCATION: (4)..(4)
<223> OTHER INFORMATION: Cysteic acid or derivative thereof
<220> FEATURE:
<223> OTHER INFORMATION: See specification as filed for detailed
      description of substitutions and preferred embodiments

<400> SEQUENCE: 1

Val Arg Gly Xaa Phe
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Cysteic acid

<400> SEQUENCE: 2

Gly Arg Gly Cys Thr Pro
1               5

<210> SEQ ID NO 3
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cysteic acid or derivative thereof
<220> FEATURE:
<223> OTHER INFORMATION: See specification as filed for detailed
      description of substitutions and preferred embodiments

<400> SEQUENCE: 3

Arg Gly Xaa
1

<210> SEQ ID NO 4
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cysteic acid or derivative thereof
<220> FEATURE:

```
<223> OTHER INFORMATION: See specification as filed for detailed
      description of substitutions and preferred embodiments

<400> SEQUENCE: 4

Arg Gly Xaa
1

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cysteic acid or derivative thereof
<220> FEATURE:
<223> OTHER INFORMATION: See specification as filed for detailed
      description of substitutions and preferred embodiments

<400> SEQUENCE: 5

Arg Gly Xaa
1

<210> SEQ ID NO 6
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cysteic acid or derivative thereof
<220> FEATURE:
<223> OTHER INFORMATION: See specification as filed for detailed
      description of substitutions and preferred embodiments

<400> SEQUENCE: 6

Arg Gly Xaa
1

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cysteic acid or derivative thereof
<220> FEATURE:
<223> OTHER INFORMATION: See specification as filed for detailed
      description of substitutions and preferred embodiments

<400> SEQUENCE: 7

Arg Gly Xaa
1

<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Cysteic acid or derivative thereof
<220> FEATURE:
<223> OTHER INFORMATION: See specification as filed for detailed
      description of substitutions and preferred embodiments

<400> SEQUENCE: 8

Arg Gly Xaa
1

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: This region may encompass 1 to 3 residues
      selected from cyclic or linear "Phe Val Ala," "Phe Leu Ala," "Phe
      Val Gly," "Phe Leu Gly," "Phe Pro Gly," "Phe Pro Ala," "Phe Val"
<220> FEATURE:
<221> NAME/KEY: MOD_RES
<222> LOCATION: (1)..(3)
<223> OTHER INFORMATION: Continued from above: or any salt of any
      combination of the D isomer or L isomer of: Arg, Gly, Cysteic,
      Phe, Val, Ala, Leu, Pro, or Thr wherein some positions may be
      absent
<220> FEATURE:
<221> NAME/KEY: MOD_RES
<222> LOCATION: (6)..(6)
<223> OTHER INFORMATION: Cysteic acid
<220> FEATURE:
<221> NAME/KEY: MOD_RES
<222> LOCATION: (7)..(9)
<223> OTHER INFORMATION: This region may encompass 1 to 3 residues
      selected from cyclic or linear "Phe Val Ala," "Phe Leu Ala," "Phe
      Val Gly," "Phe Leu Gly," "Phe Pro Gly," "Phe Pro Ala," "Phe Val"
<220> FEATURE:
<221> NAME/KEY: MOD_RES
<222> LOCATION: (7)..(9)
<223> OTHER INFORMATION: Continued from above: or any salt of any
      combination of the D isomer or L isomer of: Arg, Gly, Cysteic,
      Phe, Val, Ala, Leu, Pro, or Thr wherein some positions may be
      absent
<220> FEATURE:
<223> OTHER INFORMATION: See specification as filed for detailed
      description of substitutions and preferred embodiments

<400> SEQUENCE: 9

Xaa Xaa Xaa Arg Gly Cys Xaa Xaa Xaa
1               5

<210> SEQ ID NO 10
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cysteic acid

<400> SEQUENCE: 10

Arg Gly Cys
1
```